United States Patent
Cole

(10) Patent No.: US 10,495,973 B2
(45) Date of Patent: Dec. 3, 2019

(54) 3D PRINTED COMPOSITES FROM A SINGLE RESIN BY PATTERNED LIGHT EXPOSURES

(71) Applicant: Align Technology, Inc., San Jose, CA (US)

(72) Inventor: Michael Christopher Cole, Longmont, CO (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/024,555

(22) Filed: Jun. 29, 2018

(65) Prior Publication Data

US 2019/0033719 A1 Jan. 31, 2019

Related U.S. Application Data

(60) Provisional application No. 62/527,749, filed on Jun. 30, 2017.

(51) Int. Cl.

| | | |
|---|---|---|
| C08F 2/46 | (2006.01) | |
| C08F 2/50 | (2006.01) | |
| C08G 61/04 | (2006.01) | |
| G03F 7/20 | (2006.01) | |
| C08F 2/44 | (2006.01) | |
| C08F 2/48 | (2006.01) | |
| C08F 218/04 | (2006.01) | |
| C08F 220/18 | (2006.01) | |
| B33Y 80/00 | (2015.01) | |
| B33Y 70/00 | (2015.01) | |
| B33Y 10/00 | (2015.01) | |
| B29C 64/106 | (2017.01) | |
| A61C 7/08 | (2006.01) | |
| C08F 220/14 | (2006.01) | |
| C08F 222/14 | (2006.01) | |
| G03F 7/029 | (2006.01) | |
| B29K 105/00 | (2006.01) | |

(52) U.S. Cl.
CPC ............ *G03F 7/2002* (2013.01); *A61C 7/08* (2013.01); *B29C 64/106* (2017.08); *B33Y 10/00* (2014.12); *B33Y 70/00* (2014.12); *B33Y 80/00* (2014.12); *C08F 2/44* (2013.01); *C08F 2/48* (2013.01); *C08F 218/04* (2013.01); *C08F 220/14* (2013.01); *C08F 220/18* (2013.01); *C08F 222/14* (2013.01); *G03F 7/029* (2013.01); *G03F 7/2004* (2013.01); *B29K 2105/0002* (2013.01); *C08F 2800/20* (2013.01)

(58) Field of Classification Search
CPC ......... B33Y 70/08; B33Y 80/00; B33Y 10/00; G03F 7/2002; G03F 7/029; G03F 7/2004; B29C 64/106; B29K 2105/0002; A61C 7/08; C08F 220/14; C08F 222/14; C08F 2800/20; C08F 220/18; C08F 2/48; C08F 220/1875; C08F 218/10; C08F 2220/1825; C08F 226/12; C08F 218/04; C08F 2/44; C08F 2222/1013; C08F 2222/102; C08F 2222/21; C08F 2222/14

USPC .................................................. 522/1; 520/1

See application file for complete search history.

(56) References Cited

U.S. PATENT DOCUMENTS

| | | | |
|---|---|---|---|
| 8,921,447 B2 * | 12/2014 | Cook ........................ | C08F 2/48 522/111 |
| 2014/0061974 A1 | 3/2014 | Tyler et al. | |
| 2014/0265034 A1 | 9/2014 | Dudley | |
| 2015/0097315 A1 | 4/2015 | Desimone et al. | |
| 2015/0097316 A1 | 4/2015 | Desimone et al. | |
| 2015/0102532 A1 | 4/2015 | Desimone et al. | |

FOREIGN PATENT DOCUMENTS

| | | | | |
|---|---|---|---|---|
| WO | WO-2012061702 A1 * | 5/2012 | ................ | C08F 2/00 |
| WO | WO-2015014381 A1 | 2/2015 | | |
| WO | WO-2016149151 A1 | 9/2016 | | |
| WO | WO-2017112682 A1 | 6/2017 | | |
| WO | WO-2019006409 A1 | 1/2019 | | |

OTHER PUBLICATIONS

International search report with written opinion dated Sep. 5, 2018 for PCT/US2018/040467.
Tumbleston, et al. Additive manufacturing. Continuous liquid interface production of 3D objects. Science. Mar. 20, 2015;347(6228):1349-52. doi: 10.1126/science.aaa2397. Epub Mar. 16, 2015.

\* cited by examiner

*Primary Examiner* — Jessica Whiteley

(74) *Attorney, Agent, or Firm* — Wilson Sonsini Goodrich & Rosati

(57) ABSTRACT

Provided herein are processes for the generation of composite polymer materials utilizing a single resin. The processes utilize diffusion between a region undergoing a polymerization reaction preferentially polymerizing one monomer component and an unreactive region. Diffusion and subsequent/concurrent polymerization results in a higher concentration of the more reactive monomer component in the reacting region and a higher concentration of the less reactive monomer components in the unreactive region. The unreactive region may be later polymerized. In embodiments, photopolymerization is used and the regions are generated by a mask or other mechanism to pattern the light.

29 Claims, 7 Drawing Sheets

 Homogenous material – polymer is equally composed of monomer 1 and monomer 2.

 Composite material 1 – polymer is mostly composed of monomer 1.

 Composite material 2 – polymer is mostly composed of monomer 2.

Layer contains a composite material – 2 different polymers present.

FIG. 3

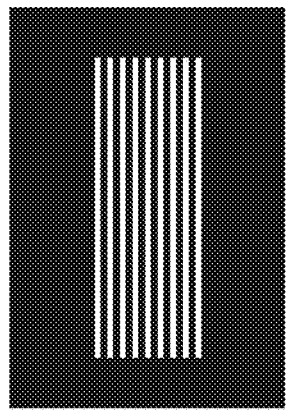 Layer 1 – One exposure to create a homogenous layer with no composite

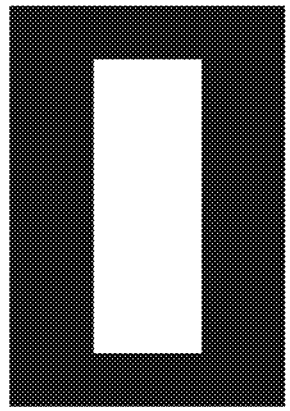 Layer 2 – 1st exposure – Create a structure of mostly polymer of mostly monomer 1

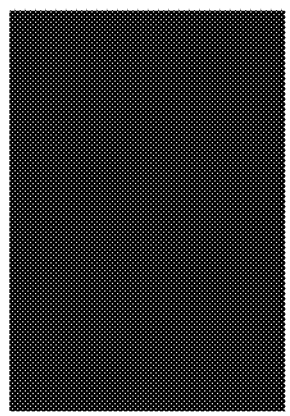

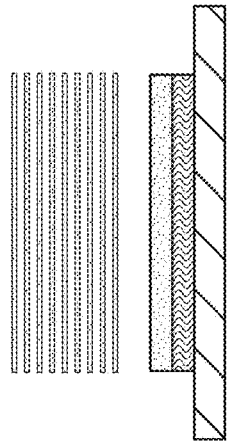

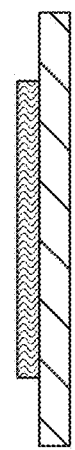

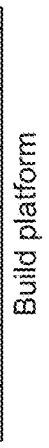

Print area

Build platform

FIG. 4

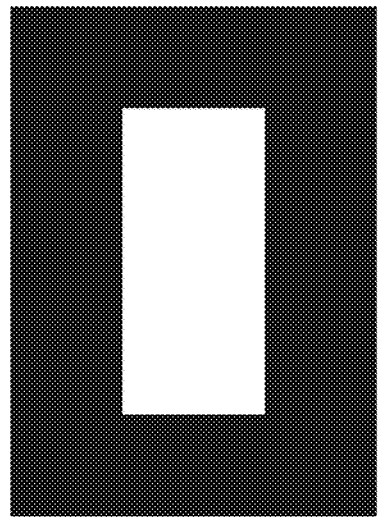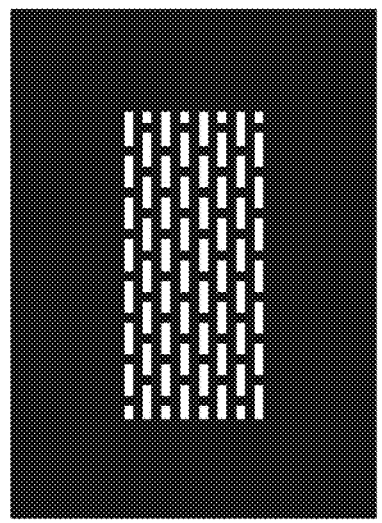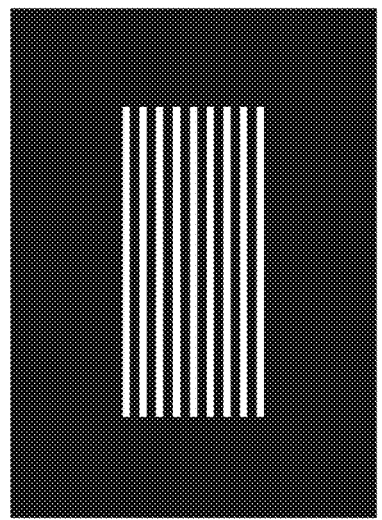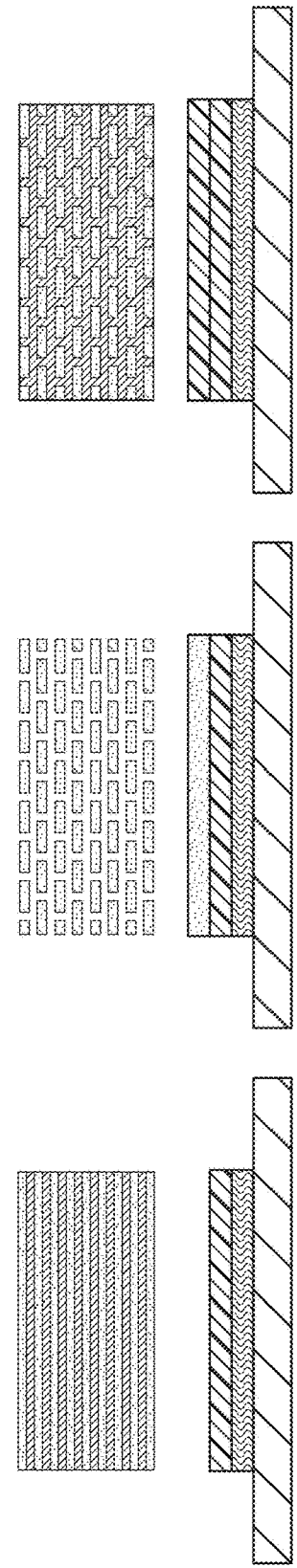
FIG. 5

3D PRINTED COMPOSITES FROM A SINGLE RESIN BY PATTERNED LIGHT EXPOSURES

CROSS-REFERENCE

This application claims the benefit of U.S. Provisional Application No. 62/527,749, filed Jun. 30, 2017, which is incorporated herein by reference in its entirety for all purposes.

BACKGROUND

Orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner. The appliance is configured to exert force on one or more teeth in order to effect desired tooth movements. The application of force can be periodically adjusted by the practitioner (e.g., by altering the appliance or using different types of appliances) in order to incrementally reposition the teeth to a desired arrangement. There remains a need for improved dental appliance fabrication.

SUMMARY

The present disclosure provides methods, systems, and devices for the generation of composite materials from a single resin using light exposure.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In various aspects, the present disclosure provides a process for making a composite polymer composition, said process comprising the steps of: providing a light polymerizable liquid composition comprising a first polymerizable component, a second polymerizable component, and a photoinitiator, wherein the light polymerizable liquid composition is characterized by a liquid ratio of the first polymerizable component to the second polymerizable component; generating a first polymer region having a first ratio of the first polymerizable component to the second polymerizable component by exposing the light polymerizable liquid composition to a first exposure of light characterized by a first exposure region; and polymerizing the light polymerizable liquid composition in a second region different than the first region and adjacent to, contacting, or overlapping with the first exposure region, wherein the second region has a second ratio of the first polymerizable component to the second polymerizable component, and wherein the liquid ratio, the first ratio, and the second ratio are different.

In some aspects, the light polymerizable liquid composition is homogenous. In certain aspects, the liquid ratio has a variation, and the variation is dependent on localization. In certain aspects, the first polymerizable component can diffuse freely through the light polymerizable liquid composition. In some aspects, the second polymerizable component can diffuse freely through the light polymerizable liquid composition.

In certain aspects, the first ratio is greater than the liquid ratio, and the liquid ratio is greater than the second ratio. In some aspects, the first ratio is greater than the second ratio, and the second ratio is greater than the liquid ratio. In certain aspects, the second ratio is greater than the liquid ratio, and the liquid ratio is greater than the first ratio. In some aspects, the second ratio is greater than the first ratio, and the first ratio is greater than the liquid ratio. In certain aspects, the liquid ratio is greater than the first ratio, and the first ratio is greater than the second ratio. In some aspects, the liquid ratio is greater than the second ratio, and the second ratio is greater than the first ratio.

In some aspects, polymerizing the light polymerizable liquid composition in the second region generates a second polymer, and wherein the first polymer is characterized by one or more different polymer properties than said second polymer. In certain aspects, the one or more different polymer properties are selected from the group consisting of: Tg, storage modulus, Young's modulus, elongation to break, elongation to yield, or any combination of these.

In certain aspects, the first polymer is characterized by a Tg that is from 2° C. to 50° C. greater than the second polymer from 5° C. to 50° C. greater than the second polymer, from 5° C. to 40° C. greater than the second polymer, from 5° C. to 30° C. greater than the second polymer, from 5° C. to 20° C. greater than the second polymer, from 5° C. to 10° C. greater than the second polymer, from 10° C. to 20° C. greater than the second polymer, from 10° C. to 50° C. greater than the second polymer, from 10° C. to 100° C. greater than the second polymer, from 1° C. to 100° C. greater than the second polymer, from 1° C. to 500° C. greater than the second polymer, from 10° C. to 500° C. greater than the second polymer, from 1° C. to 50° C. greater than the second polymer, from 1° C. to 40° C. greater than the second polymer, from 1° C. to 30° C. greater than the second polymer, from 1° C. to 20° C. greater than the second polymer, from 1° C. to 10° C. greater than the second polymer, or from 1° C. to 5° C. greater than the second polymer.

In some aspects, the first polymer is characterized by a storage modulus that is from 1 MPa to 1,000 MPa greater than the second polymer, from 1 MPa to 500 MPa greater than the second polymer, from 1 MPa to 250 MPa greater than the second polymer, from 1 MPa to 200 MPa greater than the second polymer, from 1 MPa to 100 MPa greater than the second polymer, from 1 MPa to 50 MPa greater than the second polymer, from 1 MPa to 10 MPa greater than the second polymer, from 50 MPa to 200 MPa greater than the second polymer, from 50 MPa to 500 MPa greater than the second polymer, from 50 MPa to 1,000 MPa greater than the second polymer, from 100 MPa to 1,000 MPa greater than the second polymer, from 200 MPa to 400 MPa greater than the second polymer, from 200 MPa to 600 MPa greater than the second polymer, from 200 MPa to 1,000 MPa greater than the second polymer, or from 200 MPa to 2,000 MPa greater than the second polymer.

In certain aspects, the first polymer is characterized by an elongation to break that is from 10% to 1,000% greater than the elongation to break of the second polymer, from 10% to 500% greater than the elongation to break of the second polymer, from 10% to 100% greater than the elongation to break of the second polymer, from 10% to 50% greater than the elongation to break of the second polymer, from 20% to 1,000% greater than the elongation to break of the second polymer, from 30% to 1,000% greater than the elongation to break of the second polymer, from 50% to 1,000% greater than the elongation to break of the second polymer, or from 100% to 1,000% greater than the elongation to break of the second polymer.

In some aspects, the step of exposing said light polymerizable liquid composition to said first exposure results in a polymerization induced phase separation in said light polymerizable liquid composition along one or more lateral directions. In certain aspects, the first polymerizable component and said second polymerizable component are miscible in each other. In some aspects, the second polymerizable component is partially or fully immiscible in the first polymer. In some aspects the first polymerizable component and said second polymerizable component are monofunctional monomers, polyfunctional monomers or a combination of these.

In certain aspects, the first polymerizable component comprises one or more of a methacrylate monomer, an acrylate monomer, a thiol monomer, a vinyl acetate derivative monomer, a styrene monomer, a vinyl ether monomer or a combination of these; and wherein said second polymerizable component comprises one or more of an acrylate monomer, a thiol monomer, an allyl ether monomer, a vinyl acetate derivative monomer, a vinyl chloride monomer, an acrylonitrile monomer, a vinyl ether monomer, a vinyl silane (or siloxane) monomer, a butadiene monomer, a norbornene, a maleate monomer, a fumarate monomer, an epoxide monomer, an anhydride monomer, an hydroxyl monomer a combination of these.

In some aspects the first polymerizable component is provided in said light polymerizable liquid composition at a concentration selected over the range 10 to 90 wt % and said second polymerizable component is provided in said light polymerizable liquid composition at a concentration selected over the range 10 to 90 wt %.

In certain aspects, the light polymerizable liquid composition further comprises one or more additives selected from the group consisting of additional polymerizable components, additional photoinitiators, thermal initiators, polymerization catalysts, surfactants, dispersants, viscosity modifiers, pigments, dyes, surface active compounds, fillers, particles, binders, or any combination of these.

In some aspects the first polymer, the second polymer, or both are formed by a free radical polymerization, ionic polymerization (cationic or anionic) or a combination of these. In certain aspects, the first polymer is primarily formed by free radical polymerization and wherein the second polymer is primarily formed by ionic polymerization (cationic or anionic). In some aspects, the first polymer is primarily formed by from photo-induced polymerization and wherein the second polymer is primarily formed by thermally induced polymerization.

In some aspects, the first polymerizable component and said second polymerizable component are characterized by a reactivity ratio greater than or equal to 1. In some aspects, the reactivity ratio is selected over the range of 1 to 10. In certain aspects, the reactivity ratio results from differences in a polymerization rate coefficient, concentration, functionality or any combination of these of said first polymerizable component and said second polymerizable component. In some aspects, the reactivity ratio results from differences in the solubility or diffusivity of said first polymerizable component and said second polymerizable component. In certain aspects, the reactivity ratio results from differences in oxygen inhibition, light absorption, photoinitiator concentration or any combination of these for said self-polymerization reaction of the first polymerizable component and said polymerization reaction of the first polymerizable component and the second polymerizable component.

In certain aspects, the first polymerizable component and said second polymerizable component each independently are characterized by a diffusivity in said light polymerizable liquid sufficient for a direct or additive manufacture process. In some aspects, at least a portion of said first exposure region, said second region or both independently have at least one lateral dimension less than or equal to 100 μm. In some aspects, at least a portion of said first exposure region, said second region, or both independently have at least one lateral dimension of 50 μm to 100 nm. In certain aspects, the first exposure region comprises more than one first exposure area or wherein said second region comprises more than one second exposure area. In some aspects, the first exposure region is characterized by a light intensity of less than 20 mW/cm$^2$; and wherein the second region is characterized by a light intensity equal to or greater than the light intensity of the first exposure region.

In some aspects, the first exposure region is exposed to light more than once before the second region is exposed to light. In certain aspects, the first exposure is generated via laser exposure, holography, DLP projection, optical lithography, pulsed light or an combination of these. In certain aspects, the step of polymerizing said light polymerizable liquid composition comprises exposing said light polymerizable liquid composition to a second exposure of light. In some aspects, the step of polymerizing said light polymerizable liquid composition characterized by the second region comprises exposing said light polymerizable liquid to thermal energy.

In various aspects, the process for making a composite polymer composition further comprises a method of direct or additive fabrication. In some aspects, the method of direct or additive fabrication uses a single light polymerizable liquid composition. In certain aspects, the method of direct or additive fabrication is selected from the group consisting of: a stereolithographic (SLA) technique, a digital light processing (DLP) technique, a continuous liquid interface production technique, a micro-stereolithographic (μ-SLA) technique, a two photon polymerization technique, a material jetting technique, and a combination thereof. In some aspects, the method of direct or additive fabrication generates said polymer composition comprising a composite material. In certain aspects, the method of direct or additive fabrication generates an orthodontic appliance comprising the polymer composition. In some aspects, after the second exposure is complete, a new layer is started. In certain aspects, one of more of the layers uses only 1 exposure for that layer.

In various aspects, the present disclosure provides a method of making a composite polymer composition from a single resin, the process comprising the steps of: providing a resin, the resin comprising a first monomer component and a second monomer component, the resin characterized by a resin ratio of the first monomer component to the second monomer component; initiating a polymerization reaction by exposing the resin to a first exposure of light; forming a first region having a first ratio of the first monomer component to the second monomer component; and forming a second region having a second ratio of the first monomer component to the second monomer component, wherein the resin ratio, the first ratio, and the second ratio are different.

In some aspects, the first ratio is greater than the resin ratio, and the resin ratio is greater than the second ratio. In certain aspects, the first ratio is greater than the second ratio, and the second ratio is greater than the resin ratio. In some aspects, the second ratio is greater than the resin ratio, and the liquid ratio is greater than the first ratio. In certain aspects, the second ratio is greater than the first ratio, and the first ratio is greater than the resin ratio. In some aspects, the resin ratio is greater than the first ratio, and the first ratio is greater than the second ratio.

In some aspects, the method further comprises the step of polymerizing the second monomer component. In some aspects, initiating the polymerization reaction comprises exposing the resin to a source of radiation. In certain aspects, an object is placed between the first region and the source of radiation. In some aspects, the object comprises a mask, a cover, a lens, a filter, or any combination thereof. In certain aspects, the source of radiation comprises ultraviolet light, visible light, infrared light, microwave irradiation, laser exposure, holography, DLP projection, optical lithography, pulsed light, or a combination thereof.

In certain aspects, the polymerization of the first monomer component forms a first polymer. In some aspects, polymerizing the second monomer component forms a second polymer. In certain aspects, the polymerization reaction results in a polymerization-induced phase separation along one or more lateral directions. In certain aspects, the first region and the second region are separated by a concentration gradient. In some aspects, the concentration gradient comprises the concentrations of the first monomer component and the second monomer component. In certain aspects, the concentration gradient comprises the concentration of the first polymer and the second polymer. In some aspects, the method further comprises the step of using a mask to selectively define the first region or the second region.

In some aspects, the polymerization of the second monomer component uses a secondary photopolymerization. In certain aspects, the secondary photopolymerization comprises the use of a mask, an overlapping region, a full blanket exposure, or a combination thereof. In some aspects, the secondary photopolymerization uses a second source of radiation, said source of radiation comprising ultraviolet light, visible light, infrared light, microwave irradiation, or a combination thereof. In certain aspects, the polymerization of the first monomer and the polymerization of the second monomer use the same source of radiation.

In certain aspects, the first monomer component and the second monomer component are miscible. In some aspects, the first monomer component and the second monomer component are fully miscible. In certain aspects, the second monomer component is immiscible in the first polymer. In some aspects, the second monomer component is fully immiscible in the first polymer. In certain aspects, the first monomer component is immiscible in the first polymer. In some aspects, the first monomer component is fully immiscible in the first polymer.

In some aspects, the first monomer component is monofunctional, polyfunctional, or a combination thereof. In certain aspects, the second monomer component is monofunctional, polyfunctional, or a combination thereof. In some aspects, the first monomer component comprises one or more of a methacrylate monomer, an acrylate monomer, a thiol monomer, a vinyl acetate monomer, a styrene monomer, a vinyl ether monomer, a derivative thereof, or a combination thereof. In certain aspects, the second monomer component comprises one or more of an acrylate monomer, a thiol monomer, an allyl ether monomer, a vinyl acetate monomer, a vinyl chloride monomer, an acrylonitrile monomer, a vinyl ether monomer, a vinyl silane (or siloxane) monomer, a butadiene monomer, a norbornene, a maleate monomer, a fumarate monomer, an epoxide monomer, an anhydride monomer, a hydroxyl monomer, a derivative thereof, or a combination thereof.

In certain aspects, from 10 to 90 wt % of the resin consists of the first monomer component. In some aspects, from 10 to 90 wt % of the resin consists of the second monomer component. In certain aspects, the resin further comprises an additive. In some aspects, the additive is selected from the group consisting of a polymerizable component, a photoinitiator, a thermal initiator, a polymerization catalyst, a surfactant, a dispersant, a viscosity modifier, an optical absorber, a pigment, a dye, a surface active compound, a filler, a particle, a binder, or any combination thereof.

In some aspects, the polymerization reaction comprises ionic polymerization, free radical polymerization, or a combination thereof. In certain aspects, the ionic polymerization comprises cationic polymerization, anionic polymerization, or a combination thereof. In some aspects, the first polymer is formed by free radical polymerization, ionic polymerization, photo-initiated polymerization, thermally induced polymerization, or a combination thereof. In certain aspects, the second polymer is formed by free radical polymerization, ionic polymerization, photo-initiated polymerization, thermally induced polymerization, or a combination thereof. In some aspects, greater than 50% of the first polymer is formed by free radical polymerization. In certain aspects, greater than 50% of the second polymer is formed by ionic polymerization. In some aspects, the ionic polymerization comprises cationic polymerization, anionic polymerization, or a combination thereof. In certain aspects, greater than 50% of the first polymer is formed by photo-initiated polymerization. In some aspects, greater than 50% of the second polymer is formed by thermally induced polymerization. In certain aspects, greater than 50% of the first polymer is formed by thermally induced polymerization. In some aspects, greater than 50% of the second polymer is formed by photo-initiated polymerization.

In certain aspects, the first monomer component and the second monomer component have a ratio of reactivity, and wherein the ratio of reactivity of the first monomer component to the second monomer component is from 1:1 to 1:10,000, from 1:1 to 1:5,000, from 1:1 to 1:2,500, from 1:1 to 1:1,000, from 1:1 to 1:500, from 1:1 to 1:100, from 1:1 to 1:50, from 1:1 to 1:30, from 1:1 to 1:20, from 1:1.5 to 1:10,000, from 1:1.5 to 1:5,000, from 1:1.5 to 1:2,500, from 1:1.5 to 1:1,000, from 1:1.5 to 1:500, from 1:1.5 to 1:100, from 1:1.5 to 1:50, from 1:1.5 to 1:30, from 1:1.5 to 1:20, from 1:5 to 1:10,000, from 1:5 to 1:5,000, from 1:5 to 1:2,500, from 1:5 to 1:1,000, from 1:5 to 1:500, from 1:5 to 1:100, from 1:5 to 1:50, from 1:5 to 1:30, from 1:5 to 1:20, from 1:10 to 1:10,000, from 1:10 to 1:5,000, from 1:10 to 1:2,500, from 1:10 to 1:1,000, from 1:10 to 1:500, from 1:10 to 1:100, from 1:10 to 1:50, from 1:10 to 1:30, or from 1:10 to 1:20. In some aspects, the first monomer component is from 1-fold to 10-fold more reactive than the second monomer component. In certain aspects, the first monomer component is from 1-fold to 1000-fold, from 1-fold to 500-fold, from 1-fold to 100-fold, from 1-fold to 50-fold, from 1-fold to 10-fold, from 2-fold to 1000-fold, from 2-fold to 500-fold, from 2-fold to 100-fold, from 2-fold to 50-fold, from 2-fold to 10-fold, from 3-fold to 1000-fold, from 3-fold to 500-fold, from 3-fold to 100-fold, from 3-fold to 50-fold, from 3-fold to 10-fold, from 5-fold to 1000-fold, from 5-fold to 500-fold, from 5-fold to 100-fold, from 5-fold to 50-fold, from 5-fold to 10-fold, from 10-fold to 1000-fold, from 10-fold to 500-fold, from 10-fold to 100-fold, from 10-fold to 50-fold, from 50-fold to 1000-fold, from 50-fold to 500-fold, from 50-fold to 100-fold, or from 100-fold to 1000-fold more reactive than the second monomer component. In certain aspects, the first monomer component is 2-fold to 5-fold more reactive than the second monomer component.

In certain aspects, the difference in the reactivity of the first monomer component and the reactivity of the second monomer component comprises a difference in a polymerization rate coefficient, a difference in concentration, a difference in functionality, a difference in solubility, a difference in diffusivity of the first monomer component, a difference in diffusivity of the second monomer component, or any combination thereof. In some aspects, the difference in the reactivity of the first monomer component and the reactivity of the second monomer component comprises a difference in oxygen inhibition, a difference in light absorption, a difference in photoinitator concentration, or a combination thereof.

In some aspects, the first monomer component and the second monomer component comprise a diffusivity in the resin sufficient for direct or additive manufacturing. In certain aspects, the first region has at least one lateral dimension less than or equal to 500 μm, less than or equal to 300 μm, less than or equal to 200 μm, less than or equal to 100 μm, less than or equal to 50 μm, or less than or equal to 20 μm. In some aspects, the second region has at least one lateral dimension less than or equal to 500 μm, less than or equal to 300 μm, less than or equal to 200 μm, less than or equal to 100 μm, less than or equal to 50 μm, or less than or equal to 20 μm. In certain aspects, the first region has at least one lateral dimension between 50 μm and 100 nm, between 50 μm and 250 μm, between 100 μm and 250 μm, or between 100 μm and 500 μm. In some aspects, the second region has at least one lateral dimension between 50 μm and 100 nm, between 50 μm and 250 μm, between 100 μm and 250 μm, or between 100 μm and 500 μm.

In certain aspects, the source of radiation initiates polymerization of the first monomer component in a first exposure region. In some aspects, the source of radiation initiates polymerization of the second monomer component in a second exposure region. In certain aspects, the first exposure region comprises a plurality of first exposure areas, or wherein the second exposure region comprises a plurality of second exposure areas. In some aspects, the first exposure region is exposed to a first light intensity of less than 20 mW/cm$^2$. In certain aspects, the second exposure region is exposed to a second light intensity, and wherein the second light intensity is equal to or greater than the first light intensity.

In some aspects, the first exposure region is exposed to the source of radiation before the second exposure region is exposed to the source of radiation. In certain aspects, the first exposure region is exposed to the source of radiation more than once before the second exposure region is exposed to the source of radiation. In some aspects, the source of radiation comprises a wavelength of between 300 nm and 900 nm, between 300 nm and 800 nm, between 300 nm and 700 nm, between 300 nm and 600 nm, between 300 nm and 500 nm, between 300 nm and 450 nm, between 300 nm and 400 nm, between 400 nm and 800 nm, between 350 nm and 800 nm, between 350 nm and 600 nm, or between 350 nm and 500 nm. In some aspects, the first exposure region is exposed to laser exposure, holography, DLP projection, optical lithography, pulsed light, or a combination thereof. In certain aspects, the second exposure region is exposed to laser exposure, holography, DLP projection, optical lithography, pulsed light, or a combination thereof. In certain aspects, at least one of the first exposure region and the second exposure region are exposed to more than one exposure of light. In some aspects, the second exposure region is exposed to thermal energy.

In various aspects, the method of making a composite polymer composition from a single resin further comprises the step of using a single additive manufacturing machine. In certain aspects, the single additive manufacturing machine comprises a 3D printer.

In various aspects, the method of making a composite polymer composition from a single resin further comprises the step of fabricating the composite polymer composition using additive fabrication or direct fabrication. In some aspects, the additive fabrication and/or the direct fabrication uses a single light polymerizable liquid composition. In some aspects, the additive fabrication and/or the direct fabrication comprises a stereolithographic (SLA) technique, a digital light processing (DLP) technique, a continuous liquid interface production technique, a micro-stereolithographic (μ-SLA) technique, a two photon polymerization technique, a material jetting technique, or a combination thereof.

In certain aspects, a new layer is started after the second exposure region is exposed to the source of radiation. In some aspects, one or more regions use a single exposure of radiation. In certain aspects, the composite polymer composition comprises an orthodontic appliance.

In some aspects, the first region has a vertical dimension less than or equal to 500 μm, less than or equal to 300 μm, less than or equal to 200 μm, less than or equal to 100 μm, less than or equal to 50 μm, or less than or equal to 20 μm. In certain aspects, the second region has a vertical dimension less than or equal to 500 μm, less than or equal to 300 μm, less than or equal to 200 μm, less than or equal to 100 μm, less than or equal to 50 μm, or less than or equal to 20 μm. In some aspects, the first region has a vertical dimension between 50 μm and 100 nm, between 50 μm and 250 μm, between 100 μm and 250 μm, or between 100 μm and 500 μm. In certain aspects, the second region has a vertical dimension between 50 μm and 100 nm, between 50 μm and 250 μm, between 100 μm and 250 μm, or between 100 μm and 500 μm.

In certain aspects, the resin is homogenous. In other aspects, the resin ratio has a variation, and the variation is dependent on localization. In some aspects, the first polymerizable component can diffuse freely through the resin. In certain aspects, the second polymerizable component can diffuse freely through the resin.

In various aspects, the present disclosure provides a composite material made by any one of the disclosed methods. In certain aspects, the first polymer comprises a storage modulus at least 200 MPa greater than the storage modulus of the second polymer. In some aspects, the first polymer comprises a fracture strain that is from 10% to 1,000% greater than the elongation to break of the second polymer, from 10% to 500% greater than the elongation to break of the second polymer, from 10% to 100% greater than the elongation to break of the second polymer, from 10% to 50% greater than the elongation to break of the second polymer, from 20% to 1,000% greater than the elongation to break of the second polymer, from 30% to 1,000% greater than the elongation to break of the second polymer, from 50% to 1,000% greater than the elongation to break of the second polymer, or from 100% to 1,000% greater than the elongation to break of the second polymer.

In some aspects, the strength of the composite material is greater than that of the first polymer or the second polymer. In certain aspects, the flexibility of the composite material is greater than that of the first polymer or the second polymer.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 3 provides a legend for the materials of the layers described in FIGS. 4-7.

FIG. 4 depicts the formation of the first layer of a composite material, and depicts the first exposure for the second layer of a composite material.

FIG. 5 depicts the second exposure for the second layer of a composite material, the first exposure of the third layer of a composite material, and the second exposure of the third layer of a composite material.

DETAILED DESCRIPTION

Figure 1:
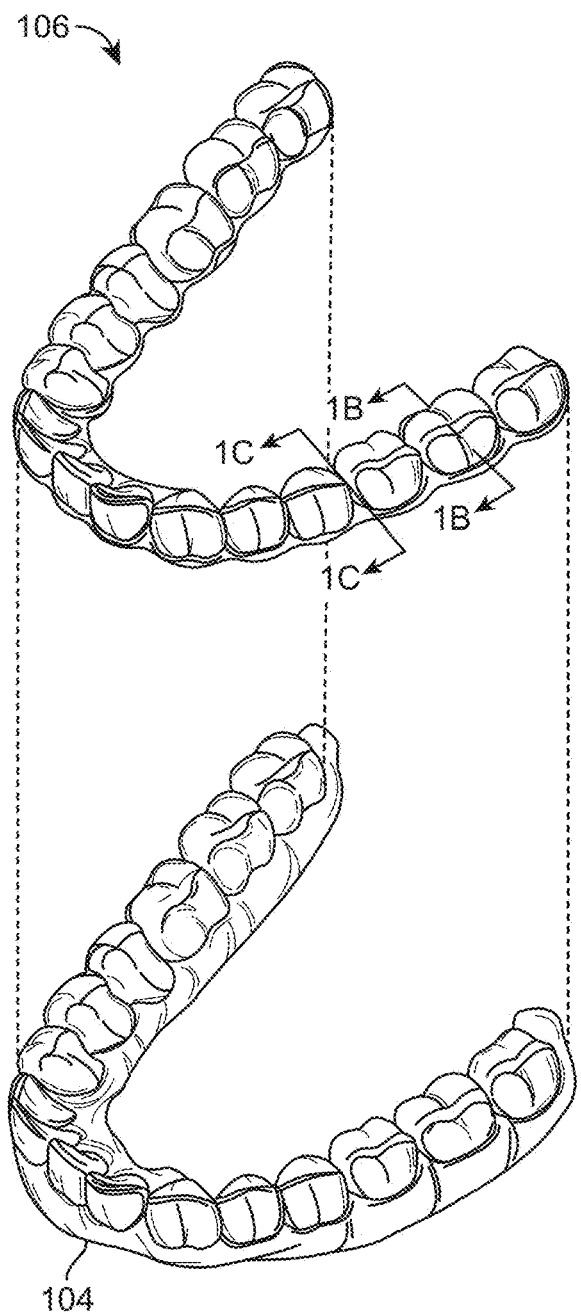
FIG. 1 depicts an exemplary dental appliance that can be formed using composite materials disclosed herein.

The present disclosure relates to methods, systems, devices, and kits for creating composite materials from a single resin. More specifically, in some aspects, the present disclosure relates to methods, systems, devices, and kits for forming composite materials having structure, wherein the structure is generated using 3D printing techniques and light exposure. In certain aspects, the methods utilize diffusion between a first region undergoing a polymerization reaction, wherein one monomer component is preferentially polymerized, and a second region wherein the monomer component less polymerized. In certain embodiments, the first region is a three-dimensional space. In some embodiments, the second region is a three-dimensional space. In preferred embodiments, the first region is defined by a 3 dimensional X,Y,Z-space. In another embodiment, the second region is defined by a 3 dimensional X,Y,Z-space.

In certain embodiments, the first region has an aspect ratio. In some embodiments, the second region has an aspect ratio. In some embodiments, both the first region and the second region have an aspect ratio. In some embodiments, the aspect ratio is greater than 1. In some embodiments, the aspect ratio comprises a diameter-width aspect ratio. In other embodiments the aspect ratio comprises a cube-volume aspect ratio.

Composite Components

Diffusion and subsequent and/or concurrent polymerization results in a higher concentration of the more reactive monomer component in the reactive first region and a higher concentration of the less reactive monomer components in the unreactive second region. The monomer components in the unreactive region may later be polymerized. In some embodiments, photopolymerization is used and the regions are generated by patterning the light. In certain embodiments, a mask is used to pattern the light. In some embodiments, a reactive region is characterized by exposure to light, while an unreactive region is characterized by a decreased or minimized exposure to light.

Polymer composites may have enhanced physical properties when compared with homopolymers of similar monomer species. For example, a composite with a first polymer having high strength (e.g., storage modulus) and a second polymer having high flexibility can result in a composite with higher toughness than a homopolymer of either monomer species.

In some embodiments, the polymer is a molecule composed of repeating structural units connected by covalent chemical bonds characterized by a substantial number of repeating units. In some embodiments, a polymer comprises equal to or greater than 10 repeating units. In certain embodiments, a polymer comprises equal to or greater than 50 repeating units. In some embodiments, a polymer comprises equal to or greater than 100 repeating units. In some embodiments, a polymer has a high molecular weight (e.g., greater than or equal to 10,000 Da). Polymers are commonly the polymerization product of one or more monomer precursors. In certain embodiments, a polymer is a homopolymer, wherein the polymer backbone consists of a single repeating monomer subunit. In some embodiments, a polymer is a copolymer, wherein the polymer comprises two or more different types of monomers linked in the same polymer. Copolymers may comprise two or more monomer subunits, and include random, block, alternating, segmented, grafted, tapered, and other copolymers.

In some embodiments, a plurality of monomeric units form an oligomer, and the oligomer is composed of repeating structural units connected by covalent chemical bonds which can be characterized by a number of repeating units less than that of a polymer (e.g., equal to or less than 10 repeating units) and/or a lower molecular weights (e.g., less than or equal to 10,000 Da) than polymers. In some embodiments, oligomers are the polymerization product of one or more monomer precursors.

In certain embodiments, a polymer is formed via a polymerization reaction of polymer precursors. In some embodiments, a resin is a viscous substance comprising polymer precursors. In some embodiments, a resin can comprise a plurality of monomer components, which can be selectively activated to form polymers (e.g., they are polymerizable components). The monomer components within the resin may undergo polymerization to form a polymer. In some embodiments, a resin comprises more than one type of monomer component. In preferred embodiments, a resin comprises a first monomer component that is more reactive than a second monomer component. In some embodiments, a resin comprises a third monomer component that can undergo polymerization.

In some embodiments, a resin is a light polymerizable liquid composition. The resin can comprise a first polymerizable component, a second polymerizable component, and a photoinitiator. In some embodiments the resin has a liquid ratio of the first polymerizable component to the second polymerizable component. In some embodiments, the liquid ratio is the same throughout the resin (e.g., a homogenous resin). In certain embodiments, the liquid ratio has localized characteristics, wherein the ratio depends on the location in the resin that the ratio is determined. As a non-limiting example, differences in density and/or immiscibility may cause separation of polymerizable components into sections, wherein one localized point of the resin can comprise a liquid ratio that is different from the liquid ratio of a different localized point within the resin. In some embodiments the resin is exposed to a region of light (a first exposure region), which can initiate polymerization and generate a first polymer region. The first polymer region has a first ratio of the first polymerizable component to the second polymerizable component. The light exposure in the first exposure region can activate the polymerization of a first polymer. In some embodiments, the first polymerizable component can diffuse freely through the resin, the second polymerizable component can diffuse freely through the resin, both the first and the second polymerizable components can diffuse freely through the resin, the first polymerizable component can diffuse freely through the first polymer, the second polymerizable component can diffuse freely through the first polymer, or both the first and the second polymerizable components can diffuse freely through the first polymer.

In some embodiments, the polymerizable components can diffuse through the resin during the polymerization of the first polymer region, thus increasing or decreasing the amount of polymerizable component in the region. As a non-limiting example, the light activated polymerization of the first polymerizable component into the first polymer in the first polymer region, combined with diffusion of the components, can result in the migration of first polymerizable components into the first polymer region, thus increasing the first ratio of the first polymerizable component to the second polymerizable component within the first polymer region, while decreasing the ratio of the first polymerizable component to the second polymerizable component in a second region (the second ratio). In some embodiments, the second region is adjacent to, contacting, or overlapping with the first exposure region, and the second region is different from the first region. In certain embodiments, the resin ratio (the liquid ratio), the first region ratio, and the second region ratio of the first polymerizable component to the second polymerizable component are different.

As a non-limiting example, a resin comprising a ratio of the first polymerizable component to the second polymerizable component of 1:1 can undergo photoinitiated polymerization in a first exposure region. A first polymer is formed from the first polymerizable material, and diffusion results in an increased amount of the first polymerizable material within the first exposure region. Following the photoinitiated polymerization, the first region has a first polymerizable component to second polymerizable component ratio (the first ratio) of 2:1. A second region that was not exposed to light has a first polymerizable component to second polymerizable component ratio (the second ratio) of 1:2. Accordingly, the first ratio (2:1) is greater than the resin ratio (1:1), and the resin ratio is greater than the second ratio (1:2).

In some embodiments, the resin ratio is greater than either the first ratio or the second ratio. As a non-limiting example, a resin comprising a ratio of the first polymerizable component to the second polymerizable component of 1:1 can undergo photoinitiated polymerization in a first exposure region. A first polymer is formed using a third polymerizable component, which causes diffusion of the first polymerizable component out of the first region. The first region has a first polymerizable component to second polymerizable component ratio of 1:2. A second exposure of light to a second region can activate polymerization of the second polymerizable component into a second polymer, and can cause diffusion of the first polymerizable component out of the second polymer region. The second polymer region has a first polymerizable component to second polymerizable component ratio of 1:3. The first polymerizable component can optionally diffuse into a third polymer region, having an increased ratio of the first polymer component to the second polymer component. Accordingly, the resin ratio (1:1) is greater than the first ratio (1:2), and the first ratio is greater than the second ratio (1:3).

In some embodiments the resin has a ratio of the first polymerizable component to the second polymerizable component of from 1:1 to 1:100,000, from 1:1 to 1:10,000, from 1:1 to 1:5,000, from 1:1 to 1:2,500, from 1:1 to 1:1,000, from 1:1 to 1:500, from 1:1 to 1:100, from 1:1 to 1:50, from 1:1 to 1:30, from 1:1 to 1:20, from 1:1.5 to 1:10,000, from 1:1.5 to 1:5,000, from 1:1.5 to 1:2,500, from 1:1.5 to 1:1,000, from 1:1.5 to 1:500, from 1:1.5 to 1:100, from 1:1.5 to 1:50, from 1:1.5 to 1:30, from 1:1.5 to 1:20, from 1:5 to 1:10,000, from 1:5 to 1:5,000, from 1:5 to 1:2,500, from 1:5 to 1:1,000, from 1:5 to 1:500, from 1:5 to 1:100, from 1:5 to 1:50, from 1:5 to 1:30, from 1:5 to 1:20, from 1:10 to 1:10,000, from 1:10 to 1:5,000, from 1:10 to 1:2,500, from 1:10 to 1:1,000, from 1:10 to 1:500, from 1:10 to 1:100, from 1:10 to 1:50, from 1:10 to 1:30, from 1:10 to 1:20, from 100,000:1 to 1:1, from 10,000:1 to 1:1, from 5,000:1 to 1:1, from 2,500:1 to 1:1, from 1,000:1 to 1:1, from 500:1 to 1:1, from 100:1 to 1:1. From 50: to 1:1, from 40:1 to 1:1, from 30:1 to 1:1, from 20:1 to 1:1, from 10:1 to 1:1, from 5:1 to 1:1, from 100,000:1 to 1:100,000, from 10,000:1 to 1:10,000, from 5,000:1 to 1:5,000, from 1,000:1 to 1:1,000, from 500:1 to 1:500, from 100:1 to 1:100, from 50:1 to 1:50, from 40:1 to 1:40, from 30:1 to 1:30, from 20:1 to 1:20, from 10:1 to 1:10, from 9:1 to 1:9, from 8:1 to 1:8, from 7:1 to 1:7, from 6:1 to 1:6, from 5:1 to 1:5, from 4:1 to 1:4, from 3:1 to 1:3, from 2:1 to 1:2, or from 1.5:1 to 1:1.5. In some embodiments, the resin has a ratio of the first polymerizable component to the second polymerizable component greater than 100,000:1. In some embodiments, the resin has a ratio of the first polymerizable component to the second polymerizable component less than 1:100,000.

In some embodiments the first region has a first ratio of the first polymerizable component to the second polymerizable component of from 1:1 to 1:100,000, from 1:1 to 1:10,000, from 1:1 to 1:5,000, from 1:1 to 1:2,500, from 1:1 to 1:1,000, from 1:1 to 1:500, from 1:1 to 1:100, from 1:1 to 1:50, from 1:1 to 1:30, from 1:1 to 1:20, from 1:1.5 to 1:10,000, from 1:1.5 to 1:5,000, from 1:1.5 to 1:2,500, from 1:1.5 to 1:1,000, from 1:1.5 to 1:500, from 1:1.5 to 1:100, from 1:1.5 to 1:50, from 1:1.5 to 1:30, from 1:1.5 to 1:20, from 1:5 to 1:10,000, from 1:5 to 1:5,000, from 1:5 to 1:2,500, from 1:5 to 1:1,000, from 1:5 to 1:500, from 1:5 to 1:100, from 1:5 to 1:50, from 1:5 to 1:30, from 1:5 to 1:20, from 1:10 to 1:10,000, from 1:10 to 1:5,000, from 1:10 to 1:2,500, from 1:10 to 1:1,000, from 1:10 to 1:500, from 1:10 to 1:100, from 1:10 to 1:50, from 1:10 to 1:30, from 1:10 to 1:20, from 100,000:1 to 1:1, from 10,000:1 to 1:1, from 5,000:1 to 1:1, from 2,500:1 to 1:1, from 1,000:1 to 1:1, from 500:1 to 1:1, from 100:1 to 1:1. From 50: to 1:1, from 40:1 to 1:1, from 30:1 to 1:1, from 20:1 to 1:1, from 10:1 to 1:1, from 5:1 to 1:1, from 100,000:1 to 1:100,000, from 10,000:1 to 1:10,000, from 5,000:1 to 1:5,000, from 1,000:1 to 1:1,000, from 500:1 to 1:500, from 100:1 to 1:100, from 50:1 to 1:50, from 40:1 to 1:40, from 30:1 to 1:30, from 20:1 to 1:20, from 10:1 to 1:10, from 9:1 to 1:9, from 8:1 to 1:8, from 7:1 to 1:7, from 6:1 to 1:6, from 5:1 to 1:5, from 4:1 to 1:4, from 3:1 to 1:3, from 2:1 to 1:2, or from 1.5:1 to 1:1.5. In some embodiments, the first ratio is greater than 100,000:1. In some embodiments, the first ratio is less than 1:100,000.

In some embodiments the second region has a second ratio of the first polymerizable component to the second polymerizable component of from 1:1 to 1:100,000, from 1:1 to 1:10,000, from 1:1 to 1:5,000, from 1:1 to 1:2,500, from 1:1 to 1:1,000, from 1:1 to 1:500, from 1:1 to 1:100, from 1:1 to 1:50, from 1:1 to 1:30, from 1:1 to 1:20, from 1:1.5 to 1:10,000, from 1:1.5 to 1:5,000, from 1:1.5 to 1:2,500, from 1:1.5 to 1:1,000, from 1:1.5 to 1:500, from 1:1.5 to 1:100, from 1:1.5 to 1:50, from 1:1.5 to 1:30, from 1:1.5 to 1:20, from 1:5 to 1:10,000, from 1:5 to 1:5,000, from 1:5 to 1:2,500, from 1:5 to 1:1,000, from 1:5 to 1:500, from 1:5 to 1:100, from 1:5 to 1:50, from 1:5 to 1:30, from 1:5 to 1:20, from 1:10 to 1:10,000, from 1:10 to 1:5,000, from 1:10 to 1:2,500, from 1:10 to 1:1,000, from 1:10 to 1:500, from 1:10 to 1:100, from 1:10 to 1:50, from 1:10 to 1:30, from 1:10 to 1:20, from 100,000:1 to 1:1, from 10,000:1 to 1:1, from 5,000:1 to 1:1, from 2,500:1 to 1:1, from 1,000:1 to 1:1, from 500:1 to 1:1, from 100:1 to 1:1. From 50: to 1:1, from 40:1 to 1:1, from 30:1 to 1:1, from 20:1 to 1:1, from 10:1 to 1:1, from 5:1 to 1:1, from 100,000:1 to 1:100,000, from 10,000:1 to 1:10,000, from 5,000:1 to 1:5,000, from 1,000:1 to 1:1,000, from 500:1 to 1:500, from 100:1 to 1:100, from 50:1 to 1:50, from 40:1 to 1:40, from 30:1 to 1:30, from 20:1 to 1:20, from 10:1 to 1:10, from 9:1 to 1:9, from 8:1 to 1:8, from 7:1 to 1:7, from 6:1 to 1:6, from 5:1 to 1:5, from 4:1 to 1:4, from 3:1 to 1:3, from 2:1 to 1:2, or from 1.5:1 to 1:1.5. In some embodiments, the second ratio is greater than 100,000:1. In some embodiments, the second ratio is less than 1:100,000.

In some embodiments, the first ratio is greater than the resin ratio, and the resin ratio is greater than the second ratio. In some embodiments, the first ratio is greater than the second ratio, and the second ratio is greater than the resin ratio. In certain embodiments, the second ratio is greater than the resin ratio, and the liquid ratio is greater than the first ratio. In some embodiments, the second ratio is greater than the first ratio, and the first ratio is greater than the resin ratio. In some embodiments, the resin ratio is greater than the first ratio, and the first ratio is greater than the second ratio. In certain embodiments, the resin ratio is greater than the second ratio, and the second ratio is greater than the first ratio.

In some embodiments, a polymerizable component is a monomer, a polymer, and/or an oligomer, which are capable of entering into polymerization through reactive groups. In some embodiments, a polymerizable component is a component of a solution or molecules in a solution that are capable of polymerizing, either with itself or with other components or molecules within the solution. In some embodiments, a first monomer, or monomer 1, is the first monomer (polymerizable component) of a X,Y,Z volume that is preferentially polymerized upon initial exposure to a source of radiation. In some embodiments, a second monomer, or monomer 2, is a monomer (polymerizable component) that is not preferentially polymerized upon initial exposure to a source of radiation. In some embodiments a first polymer, or polymer 1, comprises a majority of monomer 1. In some embodiments a second polymer, or polymer 2, comprises a majority of monomer 2. In certain embodiments the first monomer comprises a first polymerizable component. In some embodiments, the second monomer comprises a second polymerizable component.

In some embodiments, oligomers and polymer mixtures can be characterized and differentiated from other mixtures of oligomers and polymers by measurements of molecular weight and molecular weight distributions. The following definitions of molecular weight can be applied for such characterization (see: L. H. Sperling, Introduction to Physical Polymer Science, $2^{nd}$ Ed., Wiley New York (1992).). The average Molecular Weight (M) is the Average Number of Repeating Units n (or dp.) x the molecular weight or molar mass (Mi) of the repeating unit. The number-average molecular weight ($M_n$) is the arithmetic mean, representing the total weight of the molecules present divided by the total number of molecules. Molecular weight may also be measured by the weight-average molecular weight (Mw) and the z-average molecular weight Mz.

In certain embodiments, this disclosure provides methods for the generation of composite polymer compositions utilizing a single resin. In some embodiments, the single resin comprises a single type of monomer component, two types of monomer components, three types of monomer components, four types of monomer components, five types of monomer components, six types of monomer components, seven types of monomer components, eight types of monomer components, nine types of monomer components, ten types of monomer components, eleven types of monomer components, twelve types of monomer components, or more than twelve types of monomer components. In certain embodiments, the resin comprises 2 polymerizable components, 3 polymerizable components, 4 polymerizable components, 5 polymerizable components, 6 polymerizable components, 7 polymerizable components, 8 polymerizable components, 9 polymerizable components, 10 polymerizable components, 11 polymerizable components, 12 polymerizable components, 13 polymerizable components, 14 polymerizable components, 15 polymerizable components, or greater than 15 polymerizable components, The monomer components may be polymerized to form a polymer. In some embodiments, the monomer components react only with their own type to form a homopolymer. In some embodiments, the monomer components react with other types of monomer components in order to form a copolymer.

In some embodiments, the single resin comprises two monomer components, wherein one monomer component is more reactive than the other. In some embodiments, the first monomer component is at least 1.1-fold more reactive, at least 2-fold more reactive, at least 3-fold more reactive, at least 5-fold more reactive, at least 10-fold more reactive, at least 15-fold more reactive, at least 25-fold more reactive, at least 50-fold more reactive, at least 100-fold more reactive, at least 250-fold more reactive, at least 500-fold more reactive, at least 750-fold more reactive, at least 1000-fold more reactive, at least 1250-fold more reactive, at least 1500-fold more reactive, at least 2000-fold more reactive, at least 5000-fold more reactive, at least 10000-fold more reactive, at least 20000-fold more reactive, at least 50000-fold more reactive, or at least 100000-fold more reactive, than the second monomer component. In some embodiments, the first monomer component is infinitely more reactive than the second monomer component.

In some embodiments, the solution comprising a first monomer component and a second monomer component undergoes polymerization to form a polymer. In some embodiments, the first monomer component is integrated into a first polymer. In some embodiments, the second monomer component is integrated into a second polymer. In certain embodiments, a polymerization activator initiates the polymerization. In some embodiments, the polymerization activator comprises a radical initiator, a photoinitiator, a thermal initiator, a catalyst, a reactive species, or any combination thereof.

In certain embodiments, the radical initiator is selected from a halogen, a chlorine, an azo compound, azobisisobutyronitrile (AIBN), 1,1'-azobis(cyclohexanecarbonitrile) (ABCN), an organic peroxide, di-tert-butyl peroxide, benzoyl peroxide, methyl ethyl ketone peroxide, acetone peroxide, an inorganic peroxide, a peroxydisulfate salt, a transition metal catalyst, or any combination thereof.

Photoinitiators in this disclosure include those that can be activated with light and initiate polymerization of the polymerizable components of the resin. In some embodiments, the photoinitiator is a radical photoinitiator, a cationic initiator, and/or an anionic photoinitiator. In some embodiments, the photoinitiator is a Type I photoinitiator, which undergoes unimolecular bond cleavage to generate free radicals. In other embodiments the photoinitiator is a Type II photoinitiator which undergoes a bimolecular reaction to generate free radicals. Common Type I photoinitiators include, but are not limited to benzoin ethers, benzil ketals, α-dialkoxy-acetophenones, α-hydroxy-alkyl phenones and acyl-phosphine oxides. Common Type II photoinitiators include benzophenones/amines and thioxanthones/amines. Cationic initiators include aryldiazonium, diaryliodonium, and triarylsulfonium salts.

In some embodiments the photoinitiator comprises an acetophenone, 2-benzyl-2-(dimethylamino)-4'-morpholinobutyrophenone, 4'-tert-butyl-2',6'-dimethylacetophenone, 2,2-diethyoxyacetophenone, 2,2-dimethoxy-2-phenylacetophenone, 4'-ethoxyacetophenone, 3'-hydroxyacetophenone, 4'-hydroxyacetophenone, 1-hydroxycyclohexyl phenyl ketone, 2-hydroxy-4'-(2-hydroxyethoxy)-2-methylpropiophenone, 2-hydroxy-2-methylpropiophenone, 2-methyl-4'-(methylthio)-2-morpholinopropiophenone, 4'-phenoxyacetophenone, a benzyl, a benzoin, benzoin ethyl ether, benzoin methyl ether, benzoin methyl ether, 4,4'-dimethoxybenzoin, 4,4'-dimethylbenzil, a benzophenone, benzophenone-3,3',4,4'-tetracarboxylic dianhydride, 4-benzobiphenyl, 4,4'-bis(diethylamino)benzophenone, 4,4'-bis[2-(1-propenyl)phenoxy]benzophenone, 4-(diethylamino)benzophenone, 4,4'-dihydroxybenzophenone, 4-(dimethylamino)benzophenone, 3,4-dimethylbenzophenone, 3-hydroxybenzophenone, 3-hydroxybenzophenone, 4-hydroxybenzophenone, 2-methylbenzophenone, 3-methylbenzophenone, 4-methylbenzophenone, methyl benzoylformate, Michler's ketone, a cationic initiator, an anionic initiator, bis(4-tert-butylphenyl)iodonium perfluoro-1-butanesulfonate, bis(4-tert-butylphenyl) iodonium p-toluenesulfonate, bis(4-tert-butylphenyl)iodonium triflate, boc-methoxyphenyldiphenylsulfonium triflate, (4-tert-butylphenyl)diphenylsulfonium triflate, diphenyliodonium hexafluorophosphate, diphenyliodonium nitrate, diphenyliodonium p-toluenesulfonate, diphenyliodonium triflate, (4-fluorophenyl)diphenylsulfonium triflate, N-hydroxynaphthalimide triflate, N-hydroxy-5-norbornene-2,3-dicarboximide perfluoro-1-butanesulfonate, (4-iodophenyl) diphenylsulfonium triflate, (4-methoxyphenyl) diphenylsulfonium triflate, 2-(4-methoxystyryl)-4,6-bis (trichloromethyl)-1,3,5-triazine, (4-methylthiophenyl) methyl phenyl sulfonium triflate, 1-naphthyl diphenylsulfonium triflate, (4-phenoxyphenyl)diphenylsulfonium triflate, (4-phenylthiophenyl)diphenylsulfonium triflate, triarylsulfonium hexafluoroantimonate salt, triarylsulfonium hexafluorophosphate salt, triphenylsulfonium perfluoro-1-butanesulfonate, triphenylsulfonium triflate, tris (4-tetra-butylphenyl)sulfonium perfluoro-1-butanesulfonate, tris(4-tert-butylphenyl)sulfonium triflate, anthraquinone-2-sulfonic acid sodium salt, 2-tert-butylanthraquinone, camphorquinone, diphenyl(2,4,6-trimethylbenzoyl)phosphine oxide, lithium phenyl-2,4,6-trimethylbenzoylphosphinate, 9,10-phenanthrenequinone, phenylbis(2,4,6-trimethylbenzoyl)phosphine oxide, a thioxanthone, 1-chloro-4-propoxy-9H-thioxanthen-9-one, 2-chlorothioxanthen-9-one, 2,4-diethyl-9H-thioxanthen-9-one, isopropyl-9H-thioxanthen-9-one, 10-methylphenothiazine, thioxanthen-9-one, an Irgacure, TPO-L, a derivative thereof, or a combination thereof.

In some embodiments, the polymerization is initiated using an azo compound, 2,2'azobis(2-methylpropionitrile), 4,4'-azobis(4-cyanovaleric acid), 1,1'-azobis(cyclohexanecarbonitrile), azobisisobutyronitrile, benzophenone, an inorganic peroxide, ammonium persulfate, hydroxymethanesulfinic acid monosodium salt, potassium persulfate, sodium persulfate, an organic peroxide, tert-butyl hydroperoxide, tert-butyl peracetate, cumene hydroxyperoxide, 2,5-di(tert-butyl)peroxy-2,5-dimethyl-3-hexyne, dicumyl peroxide, 2,5-bis(tert-butylperoxy)-2,5-dimethylhexane, 2,5-bis(tert-butylperoxy)-2,5-dimethylhexane, 2,4-pentanedione peroxide, 1,1-bis(tert-butylperoxide)-3,3,5-trimethylcyclohexane, 1,1-bis(tert-butylperoxy)cyclohexane, benzoyl peroxide, tert-butyl peroxide, tert-butyl peroxybenzoate, TBEC, tert-butyl hydroperoxide, a derivative thereof, or a combination thereof.

In some embodiments, a thermal cure temperature is used during polymerization. In certain embodiments, the thermal cure temperature can be from −50° C. to 500° C., from −10° C. to 300° C., from −5° C. to 200° C., from 0° C. to 100° C., from 10° C. to 90° C., or from 20° C. to 80° C. In certain embodiments the amount of time a material spends at a thermal cure temperature is controlled. In some embodiments the amount of time the material spends at the thermal cure temperature is between 1 minute and 2 weeks, between 1 minute and 1 week, between 1 minute and 6 days, between 1 minute and 5 days, between 1 minute and 4 days, between 1 minute and 3 days, between 1 minute and 2 days, between 1 minute and 24 hours, between 1 minute and 12 hours, between 1 minute and 6 hours, between 1 minute and 3 hours, between 1 minute and 2 hours, between 1 minute and 1 hour, between 5 minutes and 1 hour, between 10 minutes and 1 hour, between 15 minutes and 2 hours, or between 30 minutes and 2 hours.

In some embodiments, polymerization is activated using a source of radiation. In certain embodiments, the source of radiation comprises ultraviolet light, visible light, infrared light, microwave irradiation, laser exposure, holography, DLP projection, optical lithography, pulsed light, or a combination thereof.

In some embodiments, it is preferential that an initial intensity of exposure is low in order to favorably induce polymerization of one monomer component. In some embodiments, a first exposure is used to form a first polymer. In certain embodiments, the intensity of the first exposure is between 10 nW and 100 mW, between 50 nW and 80 mW, between 100 nW and 50 mW, between 100 nW and 10 mW, between 0.1 mW and 8 mW, between 0.1 mW and 6 mW, between 0.1 mW and 4 mW, or between 0.1 mW and 2 mW.

In some embodiments, it is preferential that a second exposure has high intensity of exposure in order to induce polymerization of remaining monomers that did not undergo polymerization in the first exposure. In some embodiments, a second exposure is used to form a second polymer. In certain embodiments, the intensity of the second exposure is between 1 mW and 1000 mW, between 5 mW and 500 mW, between 5 mW and 100 mW, or between 10 mW and 100 mW.

In certain embodiments, the polymerization reaction comprises step-growth polymerization, chain-growth polymerization, radical polymerization, living polymerization, cationic addition polymerization, anionic addition polymerization, emulsion polymerization, solution polymerization, precipitation polymerization, photopolymerization, or any combination thereof. In preferred embodiments, the polymerization reaction comprises photopolymerization.

Diffusion of all the components results in a higher concentration of the more reactive monomer component in the reacting region (e.g., a first region) and a higher concentration of the less reactive monomer components in the unreactive region (e.g., a second region). In some embodiments, the reactive region (the first region) is characterized by being exposed to a source of radiation during an initial exposure. In certain embodiments, the unreactive region (the second region) is not exposed to the source of radiation during an initial exposure.

In certain embodiments, diffusion of resin components takes place. In some embodiments, the first monomer component and the second monomer component diffuse through the first polymer during the polymerization of the first polymer. In some embodiments, as the first monomer components are polymerized into the first polymer, diffusion of the first monomer component slows. In certain embodiments, only the second monomer component undergoes diffusion through the first polymer. In some embodiments, the diffusion creates regions having higher concentration of components. For example, a region-specific polymerization reaction that polymerizes a first monomer component but not a second monomer component would produce the first polymer in the specific regions, while the second monomer component diffused toward other regions. Accordingly, a region of the composite material may comprise greater than 0.1% of a first monomer component, greater than 5% of a first monomer component, greater than 10% of a first monomer component, greater than 20% of a first monomer component, greater than 30% of a first monomer component, greater than 40% of a first monomer component, greater than 50% of a first monomer component, greater than 60% of a first monomer component, greater than 70% of a first monomer component, greater than 80% of a first monomer component, greater than 90% of a first monomer component, or greater than 95% of a first monomer component by weight. The first monomer component may partially or fully undergo polymerization, and therefore a region of the composite material may comprise greater than 50% of a first polymer, greater than 60% of a first polymer, greater than 70% of a first polymer, greater than 80% of a first polymer, greater than 90% of a first polymer, or greater than 95% of a first polymer by weight.

The diffusion of a second monomer component out of the first region can result in a lowering of the amount of the second monomer component in the first region. In some embodiments, a region of the composite material may comprise less than 100% of a second monomer component, less than 95% of a second monomer component, less than 90% of a second monomer component, less than 80% of a second monomer component, less than 70% of a second monomer component, less than 60% of a second monomer component, less than 50% of a second monomer component, less than 40% of a second monomer component, less than 30% of a second monomer component, less than 20% of a second monomer component, less than 10% of a second monomer component, or less than 5% of a second monomer component by weight. The unreactive region may be later polymerized. The second monomer component may partially or fully undergo polymerization, and therefore a region of the composite material may comprise less than 50% of a second polymer, less than 40% of a second polymer, less than 30% of a second polymer, less than 20% of a second polymer, less than 10% of a second polymer, or less than 5% of a second polymer by weight.

In some embodiments, a composite material can undergo copolymerization in selective regions. In certain embodiments, a composite material undergoes copolymerization based on exposure to a source of radiation. In certain embodiments, diffusion of resin components takes place wherein the first monomer component and the second monomer component diffuse through the resin during the polymerization to form a copolymer comprising the first monomer component and the second monomer component. Accordingly, selective polymerization can provide regions comprising a copolymer, while regions that are not exposed to the source of radiation comprise less to no copolymer. In some embodiments, the diffusion creates regions having higher concentration of components or copolymer. For example, a region-specific polymerization reaction that polymerizes a first monomer component and a second monomer component would produce the copolymer in the specific regions, while other resin components diffused toward other regions. The first monomer component and the second monomer component may partially or fully undergo polymerization, and therefore a region of the composite material may comprise greater than 50% of a first copolymer, greater than 60% of a first copolymer, greater than 70% of a first copolymer, greater than 80% of a first copolymer, greater than 90% of a first copolymer, or greater than 95% of a first copolymer by weight.

In some embodiments, the irradiation of a region of the resin provides a change in the percentage of monomer presence, or a corresponding change in the presence of its corresponding polymer. In certain embodiments, this enrichment of monomer components or polymer uses a source of radiation. In some embodiments, a higher percentage of one monomer component is present in a region than what would be expected by bulk cure conditions. In preferred embodiments, the percentage change is greater than 10% (mole percentage) from initial resin values. In some embodiments, the percentage change is about 5% or greater than 5% from initial resin values. In certain embodiments, the percent change is greater than 20%, greater than 30%, greater than 40%, greater than 50%, greater than 60%, greater than 70%, greater than 80%, greater than 90%, greater than 95%, or greater than 98% (mole percentage) from initial resin values. As a non-limiting example, a resin comprising an initial amount of 60% Monomer A and 40% Monomer B is polymerized to provide a bulk copolymerized material having an average of a 60% Monomer A and 40% Monomer B in the bulk cured copolymer. In comparison, using the methods disclosed herein, a region-specific preferential polymerization of the same resin may produce a copolymer having an average composition of 50% Monomer A and 50% Monomer B, which would be a 17% decrease in the concentration of Monomer A in the region, while monomer B would experience a 25% increase in average regional copolymer composition. The percentage can be based on an initial and final molar percentage for monomer concentration in the starting monomer mix and for the monomer concentration incorporated into a copolymer for a defined region of space. In some embodiments, the concentration or composition of starting monomer mixtures and final polymer composition are described by weight percentages.

In some embodiments, the composite material comprises a first monomer component and a second monomer component, wherein the two monomer components have different reactivity. The reactivity is a determined value. A monomer's reactivity ratio is a value that compares the monomer's reactivity with a second monomer. Reactivity ratios of monomer components are available in the art (see, e.g., G. Odian, Principles of Polymerization, 4$^{th}$ Ed., 2004, which is incorporated herein by reference). In some embodiments, a reactivity ratio or ratio of reactivity refers to the ratio of a rate coefficient for the reaction of a monomer with itself to the rate coefficient of the monomer with that of a different monomer. In some embodiments, reactivity ratio is defined by the formula:

$$R = \frac{k_{11}}{k_{12}}$$

wherein $k_{11}$ is the rate coefficient corresponding to a reaction of monomer 1 (or a polymer with monomer 1 in a terminal position) with monomer 1 and $k_{12}$ is the rate constant coefficient to a reaction of monomer 1 (or a polymer with monomer 1 in a terminal position) with monomer 2. In certain embodiments, reactivity ratios depend on temperature, concentration, and other physical conditions.

In certain embodiments, the reactivity ratio between the first monomer component and the second monomer component is greater than or equal to one. In some embodiments, the reactivity ratio between the first monomer component and the second monomer component is greater than or equal to 10, greater than or equal to 20, greater than or equal to 30, greater than or equal to 50, greater than or equal to 100, greater than or equal to 500, greater than or equal to 1000, greater than or equal to 5000, greater than or equal to 10000, greater than or equal to 50000, or greater than or equal to 100000. In some embodiments, the reactivity ratio between the first monomer component and the second monomer component is from 1 to 10, from 1 to 20, from 1 to 30, from 1 to 50, from 1 to 100, from 1 to 500, from 1 to 1000, from 1 to 5000, from 1 to 10000, from 1 to 50000, from 1 to 100000, from 2 to 10, from 2 to 20, from 2 to 30, from 2 to 50, from 2 to 100, from 2 to 500, from 2 to 1000, from 2 to 5000, from 2 to 10000, from 2 to 50000, or from 2 to 100000.

In some embodiments, the first monomer component and the second monomer component have a ratio of reactivity, and the ratio of reactivity of the first monomer component to the second monomer component is greater than or equal to 1:1, greater than or equal to 1:1.1, greater than or equal to 1:1.25, greater than or equal to 1:1.5, greater than or equal to 1:2, greater than or equal to 1:5, greater than or equal to 1:10, greater than or equal to 1:20, greater than or equal to 1:30, greater than or equal to 1:50, greater than or equal to 1:100, greater than or equal to 1:500, greater than or equal to 1:1000, greater than or equal to 1:5000, greater than or equal to 1:10000, greater than or equal to 1:50000, or greater than or equal to 1:100000. In certain embodiments, the first monomer component is from 1-fold to 10000-fold, from 1-fold to 5000-fold, from 1-fold to 1000-fold, from 1-fold to 500-fold, from 1-fold to 100-fold, from 1-fold to 50-fold, from 1-fold to 10-fold, from 2-fold to 10000-fold, from 2-fold to 1000-fold, from 2-fold to 500-fold, from 2-fold to 100-fold, from 2-fold to 50-fold, from 2-fold to 10-fold, from 3-fold to 1000-fold, from 3-fold to 500-fold, from 3-fold to 100-fold, from 3-fold to 50-fold, from 3-fold to 10-fold, from 5-fold to 1000-fold, from 5-fold to 500-fold, from 5-fold to 100-fold, from 5-fold to 50-fold, from 5-fold to 10-fold, from 10-fold to 1000-fold, from 10-fold to 500-fold, from 10-fold to 100-fold, from 10-fold to 50-fold, from 50-fold to 1000-fold, from 50-fold to 500-fold, from 50-fold to 100-fold, or from 100-fold to 1000-fold more reactive than the second monomer component.

In some embodiments, a difference in reactivity comprises a difference in a polymerization rate coefficient, a difference in concentration, a difference in functionality (such as mono-functional, di-functional, tri-functional, etc.), a difference in solubility, a difference in diffusivity of the first monomer component, a difference in diffusivity of the second monomer component, or any combination thereof. In some embodiments, techniques can be used to change the composition of the first polymer in comparison to the composition of the second polymer. In certain embodiments, the composition of the first polymer is determined by differences in reactivity between the first monomer and the second monomer. In specific embodiments, a difference in reactivity comprises a difference in oxygen inhibition, a difference in light absorption, a difference in photoinitator concentration, a difference in monomer concentration, temperature, monomer solubilities, polymer solubilities, or a combination thereof.

In some embodiments, photopolymerization is used and the regions are generated by a mask, a photomask, or cover protecting the unreactive region from a light source. In certain embodiments, the mask or cover comprises a pattern, thereby forming patterned regions of polymerization on the layer. In certain embodiments, the mask comprises a plurality of lines, a plurality of parallel lines, a plurality of brick shapes, a plurality of circular holes, a plurality of perpendicular lines forming a hatched pattern, or a combination thereof. In some embodiments, the mask comprises regions that allow unimpeded radiation, wherein the smallest axis of the region is from 20 nm to 100 microns in size, from 20 nm to 10 microns in size, from 20 nm to 1 micron in size, from 20 nm to 500 nm in size, from 20 nm to 300 nm in size, from 100 nm to 100 microns in size, from 100 nm to 10 microns in size, from 100 nm to 1 micron in size, from 100 nm to 500 nm in size, from 200 nm to 100 microns in size, from 200 nm to 50 microns in size, from 200 nm to 25 microns in size, from 200 nm to 5 microns in size, from 200 nm to 1 micron in size, from 1micron to 100 microns in size, from 1 to 50 microns in size, from 1 to 40 microns in size, from 1 to 30 microns in size, from 1 to 20 microns in size, from 1 to 10 microns in size, from 2 to 100 microns in size, from 2 to 50 microns in size, from 2 to 25 microns in size, from 2 to 10 microns in size, from 4 to 100 microns in size, from 4 to 50 microns in size, from 4 to 40 microns in size, from 4 to 20 microns in size, form 4 to 10 microns in size, from 6 to 100 microns in size, from 6 to 50 microns in size, from 6 to 25 microns in size, from 6 to 20 microns in size, from 10 to 100 microns in size, or from 10 to 50 microns in size.

In certain embodiments, photopolymers are fabricated by "vat" processes in which light is used to selectively cure a section or portion of resin in a vat or reservoir. Each layer of the object being fabricated may be selectively exposed to light in a single exposure or by scanning a beam of light across the layer. Specific techniques include stereolithography (SLA), Digital Light Processing (DLP), holographic projection, and two photon-induced photopolymerization (TPIP).

Processes of Manufacture

Advances in three-dimensional (3D) printing and/or additive manufacturing provide an ability to quickly and efficiently generate polymer-based orthodontic appliances. Most 3D printing techniques rely on a layer by layer generation technique, which makes it difficult to produce devices which have multiple materials or compounds. In certain embodiments herein, multiple layers in an orthodontic appliance can be formed that each provide different physical properties. In some embodiments herein, at least one layer provides a mechanical strength (modulus) required to apply an orthodontic force necessary to adjust a patient's tooth while at least one other layer provides elasticity so that the composite material is not easily broken or damaged.

In some embodiments, additive manufacturing refers to a variety of technologies which fabricate three-dimensional objects directly from digital models through an additive process. In some aspects, successive layers of material are deposited and cured in place. In some embodiments, 3D printing can be used to fabricate appliances. In certain embodiments, 3D printing can be used to fabricate orthodontic appliances. In some embodiments, 3D printing involves jetting or extruding one or more materials onto a build surface in order to form successive layers of the object geometry.

The various embodiments of the orthodontic appliances presented herein can be fabricated using a composite material in a wide variety of ways. In some embodiments, the orthodontic appliances herein (or portions thereof) can be produced using direct fabrication, such as additive manufacturing techniques (also referred to herein as "3D printing"). Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry. Any of these additive manufacturing methods can be used in conjunction with the present invention; for example, by applying light at some portion of the process to cure the material being deposited.

Alternatively or in combination, the appliance can be fabricated with machining such as an appliance fabricated from a block of material with computer numeric control machining. The system can comprise one or more processors configured with instructions to: determine a movement path to move one or more teeth from an initial arrangement to a target arrangement; determine an appliance geometry for an orthodontic appliance comprising a shell and an integrally formed component; and generate instructions for direct fabrication of the orthodontic appliance, wherein the instructions are configured to cause direct fabrication of the shell using a resin comprising a first monomer component and direct fabrication of the integrally formed component using a second, different monomer component in the resin. For example, in some embodiments, instructions can be configured to cause direct fabrication of both the shell and the integrally formed component using a resin comprising both the first monomer component and the second monomer component. Selective application of light to one of the shell or the integrally formed component, in accordance with techniques disclosed herein, can produce polymer compositions of the shell and integrally formed component that differ in their respective percentages of first and second monomer components. For example, the shell can have an increased (or alternatively decreased) percentage of the first monomer component relative to the one or both of the integrally formed component and the resin, and a decreased (or alternatively increased) percentage of the second monomer component relative to the one or both of the integrally formed component and the resin.

In some embodiments, continuous direct fabrication methods for photopolymers are used herein. For example, a direct fabrication process can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved.

In some embodiments, a continuous direct fabrication method utilizes a heliolithography approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

In certain embodiments, continuous liquid interface production of 3D objects is used herein. Such methods have been reported in J. Tumbleston et al. (Science, 2015, 347

(6228), pp 1349-1352), which is hereby incorporated by reference in its entirety for description of the process. In some embodiments, continuous direct fabrication methods involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In some embodiments, the direct fabrication methods provided herein build up the composite material geometry in a layer-by-layer fashion, with successive layers being formed in discrete build steps. Alternatively or in combination, direct fabrication methods that allow for continuous build-up of composite material geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety. Patterned light can be applied during the fabrication process as a way to create a composite material as part of the extruded material, for example.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an appliance or a portion thereof. In certain embodiments, the appliance is an orthodontic appliance. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of an appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of an appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed. In some embodiments, a multi-material direct fabrication method can involve forming an object from multiple monomer components in a single resin using sequential manufacturing steps. For instance, a first portion of an object can be formed from a first selective polymerization of a first monomer with any of the polymerization and fabrication methods herein, then a second portion of the object can be formed from the same resin in accordance with the polymerization and curing methods disclosed herein, and so on, until the entirety of the object has been formed.

Direct fabrication can provide various advantages compared to other manufacturing approaches. For instance, in contrast to indirect fabrication, direct fabrication permits production of an appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an appliance with feature sizes of less than or equal to about 5 µm, or within a range from about 5 µm to about 50 µm, or within a range from about 20 µm to about 50 µm.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables. Increased temperature during the light exposure stage can aid in the use of higher viscosity materials than one would normally be able to use in a vat-style process. For example, temperatures greater than 50° C. can be useful. In some instances temperatures can range from 50° C. to 100° C. In some embodiments, the vat temperature can be greater than 100° C., for resins with sufficient stability.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, an appliance includes a built-in layer or coating integrally formed with the appliance shell by direct fabrication. The layer or coating can be located on one or more of a buccal surface, lingual surface, occlusal surface, exterior surface, and/or interior surface of the shell. The layer or coating can be formed from one or more materials configured to provide additional functionality to the appliance. For example, the layer or coating can be formed from a moisture resistant material, e.g., in order to act as a sealant to reduce stress relaxation of the appliance associated with water absorption. As another example, the layer or coating can be formed from a material that resists or reduces staining. In another example, the layer or coating can be used to reduce friction between the appliance, the patient's teeth and/or another device. In some embodiments, a protective layer or coating is integrally formed into the occlusal surfaces of an appliance to protect the appliance, the patient's teeth, and/or another device, e.g., from grinding, pressure, and interference. In yet another example, the layer or coating can incorporate therapeutic agents or functional agents for drug delivery, flavoring, etc. The direct fabrication methods herein allow such layers or coatings to be formed with the shell in a single processing step.

Composite Materials

In some embodiments, polymer composites have enhanced physical properties when compared with homopolymers of similar monomer species. For example, a composite material comprising a first polymer having high strength (e.g., high storage modulus) and a second polymer having high flexibility can form a composite with higher strength and flexibility than a homopolymer of either monomer species.

In some embodiments, the step of exposing the light polymerizable liquid composition to the first exposure results in a polymerization-induced phase separation in the light polymerizable liquid composition along one or more lateral directions. In some embodiments, the phase separation results in a concentration gradient between the two polymer regions, but separation between the two polymerizable components in the lateral dimensions still occurs. In some embodiments, the lateral dimension is a length or area characterized by the x-axis, the y-axis or both the x- and y-axes as show in FIG. 7. In some embodiments, lateral dimension corresponds to the axes defined by the print area of an additive manufacturing devices, while the vertical dimension (z-axis) refers to the direction in which layers are added.

As a non-limiting example, a resin comprising a first monomer component and a second monomer component that is exposed to a source of radiation can undergo polymerization of a first polymer. The concentration of the first polymer can be highest at the point nearest the radiation source. Subsequent polymerization to form the second polymer will be more highly concentrated at a point further from the radiation source. Accordingly, a gradient exists between the first polymer and the second polymer, but separation between the two components is present. If the light source is placed in a lateral direction, the gradient can form in a lateral direction as well.

In some embodiments, the step of exposing the light polymerizable liquid composition to the first exposure results in a polymerization-induced phase separation in the light polymerizable liquid composition along a vertical direction. In some embodiments, the phase separation results in a concentration gradient between the two polymer regions, but separation between the two polymerizable components in the vertical dimension still occurs. In some embodiments, the lateral dimension is a length or area characterized by the x-axis, the y-axis or both the x- and y-axes as show in FIG. 7. In some embodiments, lateral dimension corresponds to the axes defined by the print area of an additive manufacturing devices, while the vertical dimension (z-axis) refers to the direction in which layers are added.

As a non-limiting example, a resin comprising a first monomer component and a second monomer component that is exposed to a source of radiation can undergo polymerization of a first polymer. The concentration of the first polymer can be highest at the point nearest the radiation source. Subsequent polymerization to form the second polymer will be more highly concentrated at a point further from the radiation source. Accordingly, a gradient exists between the first polymer and the second polymer, but separation between the two components is present. That is, the two polymers are different in composition and have different material properties. If the light source is placed in a vertical direction, the gradient can form in a vertical direction as well.

In some embodiments, the first monomer component comprises an an acrylic monomer, an acrylamide, a methacrylamide, an acrylonitrile, a bisphenol acrylic, a carbohydrate, a fluorinated acrylic, a maleimide, an acrylate, 4-acetoxyphenethyl acrylate, acryloyl chloride, 4-acryloylmorpholine, 2-(acryloyloxy)ethyl]trimethylammonium chloride, 2-(4-benzoyl-3-hydroxyphenoxy)ethyl acrylate, benzyl 2-propylacrylate, butyl acrylate, tert-butyl acrylate, 2[[(butylamino)carbonyl]oxy]ethyl acrylate, tert-butyl 2-bromoacrylate, 2-carboxyethyl acrylate, 2-chloroethyl acrylate, 2-(diethylamino)ethyl acrylate, di(ethylene glycol) ethyl ether acrylate, 2-(dimethylamino)ethyl acrylate, 3-(dimethylamino)propyl acrylate, dipentaerythriol penta-/hexa-acrylate, ethyl acrylate, 2-ethylacryloyl chloride, ethyl 2-(bromomethyl)acrylate, ethyl cis-(beta-cyano) acrylate, ethylene glycol dicyclopentenyl ether acrylate, ethylene glycol methyl ether acrylate, ethylene glycol phenyl ether acrylate, ethyl 2-ethylacrylate, 2-ethylhexyl acrylate, ethyl 2-propylacrylate, ethyl 2-(trimethylsilylmethyl) acrylate, hexyl acrylate, 4-hydroxybutyl acrylate, 2-hydroxyethyl acrylate, 2-hydroxy-3-phenoxypropyl acrylate, hydroxypropyl acrylate, isobornyl acrylate, isobutyl acrylate, isodecyl acrylate, isooctyl acrylate, lauryl acrylate, methyl 2-acetamidoacrylate, methyl acrylate, a methylene malonate (e.g., dibutyl methylene malonate, dihexyl methylene malonate, or dicyclohexyl methylene malonate), a methylene malonate macromerer (e.g, a polyester of 2-methylenemalonate such as Forza B3000 XP), methyl α-bromoacrylate, methyl 2-(bromomethyl)acrylate, methyl 2-(chloromethyl)acrylate, methyl 3-hydroxy-2-methylenebutyrate, methyl 2-(trifluoromethyl)acrylate, octadecyl acrylate, pentabromobenzyl acrylate, pentabromophenyl acrylate, pentafluorophenyl acrylate, poly(ethylene glycol) diacrylate, poly(ethylene glycol) methyl ether acrylate, poly(propylene glycol) acrylate, epoxidized soybean oil acrylate, 3-sulfopropyl acrylate, tetrahydrofuryl acrylate, 2-tetrahydropyranyl acrylate, 3-(trimethoxysilyl)propyl acrylate, 3,5,5-trimethylhexyl acrylate, 10-undecenyl acrylate, urethane acrylate, urethane acrylate methacrylate, tricylcodecane diacrylate, isobornyl acrylate, a methacrylate, allyl methacrylate, benzyl methacrylate, (2-boc-amino)ethyl methacrylate, tert-butyl methacrylate, 9H-carbazole-9-ethylmethacrylate, 3-chloro-2-hydroxypropyl methacrylate, cyclohexyl methacrylate, 1,10-decamethylene glycol dimethacrylate, ethylene glycol dicyclopentenyl ether methacrylate, ethylene glycol methyl ether methacrylate, 2-ethylhexyl methacrylate, furfuryl methacrylate, glycidyl methacrylate, glycosyloxyethyl methacrylate, hexyl methacrylate, hydroxybutyl methacrylate, 2-hydroxy-5-N-methacrylamidobenzoic acid, isobutyl methacrylate, methacryloyl chloride, methyl methacrylate, mono-2-methacryloyloxy)ethyl succinate, 2-N-morpholinoethyl methacrylate, 1-naphthyl methacrylate, pentabromophenyl methacrylate, phenyl methacrylate, pentabromophenyl methacrylate, TEMPO methacrylate, 3-sulfopropyl methacrylate, triethylene glycol methyl ether methacrylate, 2-[(1',1',1'-trifluoro-2'-(trifluoromethyl)-2'Ohdroxy)propyl]-3-norbornyl methacrylate, 3,3,5-trimethylcyclohexyl methacrylate, (trimethylsilyl)methacrylate, vinyl methacrylate, isobornyl methacrylate, bisphenol A dimethacrylate, an Omnilane OC, tert-butyl acrylate, isodecyl acrylate, tricylcodecane diacrylate, a polyfunctional acrylate, N,N'-methylenebisacrylamide, 3-(acryloyloxy)-2-hydroxypropyl) methacrylate, bis[2-(methacryloyloxy) ethyl]phosphate, 1,3-butanedioldiacrylate, 1,4-butanediol diacrylate, diurethane dimethacrylate, N,N'-ethylenebis (acrylamide), glycerol 1,3-diglycerolate diacrylate, 1,6-hexanediol diacrylate, hydroxypivalyl hydroxypivalate bis [6-(acryloyloxy)hexanoate], neopentyl glycol diacrylate, pentaerythritol diacrylate, 1,3,6-triacryloyl hexahydro-1,3,5-triazine, trimethlolpropane ethoxylate, tris[2-(acryloyloxy)ethyl]isocyanurate, any derivative thereof, or a combination thereof.

In certain embodiments, the second monomer component comprises a vinyl ester, vinyl acetate, vinyl benzoate, vinyl 4-tert-butylbenzoate, vinyl chloroformate, vinyl cinnamate, vinyl decanoate, vinyl neodecanoate, vinyl neononanoate, vinyl pivalate, vinyl propionate, vinyl stearate, vinyl trifluoroacetate, vinyl valerate, vinyl laurate, isobutyl vinyl ether, Omnilane OC 1005, Omnilane OC 3005, Omnilane OC 2005, a methylene malonate (e.g., dibutyl methylene malonate, dihexyl methylene malonate, or dicyclohexyl methylene malonate), a methylene malonate macromerer (e.g., a polyester of 2-methylenemalonate such as Forza B3000 XP), an anhydride, hexahydro-4-methylphthalic anhydride, cis-aconitic anhydride, s-acetylmercaptosuccinic anhydride, 4-amino-1,8-naphthalic anhydride, endo-bicyclo [2.2.2]oct-5-ene-2,3-dicarboxylic anhydride, 3,3'4,4'-biphenyltetracarboxylic dianhydride, isatoic anhydride, 5-bromoisatoic anhydride, bromomaleic anhydride, 4-bromo-1,8-naphthalic anhydride, citraconic anhydride, crotonic anhydride, 1,2-cyclohexanedicarboxylic anhydride, cyclopentene dicarboxylic anhydride, 2,3-dichloromaleic anhydride, 3,6-dichlorophthalic anhydride, diethylenetriaminepentaacetic dianhydride, 3,6-difluorophthalic anhydride, diglycolic anhydride, 2,2-dimethylglutaric anhydride, 3,3-dimethylglutaric anhydride, diphenic anhydride, (2-dodecen-1-yl)succinic anhydride, glutaric anhydride, hexafluoroglutaric anhydride, homophthalic anhydride, 3-hydroxyphthalic anhydride, isatoic anhydride, maleic anhydride, 3-methylglutaric anhydride, naphthalic anhydride, 3-nitrophthalic anhydride, 2,5-oxazolidinedione, phenylsuccinic anhydride, phenylmaleic anhydride, 2,3-pyrazinedicarboxylic anhydride, pyromellitic dianhydride, succinic anhydride, tetrabromopthalic anhydride, 3,4,5,6-tetramethyleneglutaric anhydride, trimellitic anhydride, 2-(triphenylphosphoranylidene)succinic anhydride, vinyl tert-butyl benzoate, divinyl adipate, any derivative thereof, or a combination thereof.

In some embodiments, a third monomer component is provided. In some embodiments, the third monomer component acts to bind the first monomer component and the second monomer component into a cohesive composite material. In certain embodiments, the third monomer component is an elastomer. In certain embodiments, the third monomer component comprises an Exothane, urethane dimethacrylate, Exothane 9, Exothane 10, Exothane 8, Exothane 26, Exothane 24, Exothane 32, Exothane 108, Exothane 126, a methylene malonate (e.g., dibutyl methylene malonate, dihexyl methylene malonate, or dicyclohexyl methylene malonate), a methylene malonate macromerer (e.g, a polyester of 2-methylenemalonate such as Forza B3000 XP), urethane epoxy methacrylate, tert-butylacrylate, an epoxide monomer, allyl glycidyl ether, bis[4-(glycidyloxy)phenyl]methane, 1,3-butadiene diepoxide, 1,4-butanediol diglycidyl ether, 1,4-butanediol diglycidyl ether, butyl glycidyl ether, tert-butyl glycidyl ether, 4-chlorophenyl glycidyl ether, cyclohexene oxide, cyclopentene oxide, dicyclopentadiene dioxide, 1,2,5,6-diepoxycyclooctane, 1,2,7,8-diepoxyoctane, diglycidyl 1,2-cyclohexanedicarboxylate, N,N-diglycidyl-4-glycidyloxyaniline, 1,2-epoxybutane, cis-2,3-epoxybutane, 3,4-epoxy-1-butene, 3,4-epoxycyclohexylmethyl 3,4-epoxycyclohexanecarboxylate, 1,2-epopxydodecane, 1,2-epoxyhexadecane, 1,2-epoxyhexane, 1,2-epoxy-5-hexene, 1,2-epoxy-2-methylpropane, exo-2,3-epoxynorbornane, 1,2-epoxyoctane, 1,2-epoxypentane, 1,2-epoxy-3-phenoxypropane, 1,2-epoxy-3-phenoxypropane, (2,3-epoxypropyl)benzene, N-(2,3-epoxypropyl)phthalimide, exo-3,6-epoxy-1,2,3,6-tetrahydrophthalic anhydride, 3,4-epoxytetrahydrothiophene, 2-ethylhexyl glycidyl ether, furfuryl glycidyl ether, glycerol diglycidyl ether, glicidyl isopropyl ether, glicidyl 4-methoxyphenyl ether, isophorone oxide, 4,4'-methylenebis(N,N-diglycidylaniline), 2-methyl-2-vinyloxirane, neopentyl glycol diglycidyl ether, α-pinene oxide, propylene oxide, resorcinol diglycidyl ether, cis-stillbene oxide, styrene oxide, tetraphenylolethane glycidyl ether, tris(2,3-epoxypropyl) isocyanurate, urethane epoxy methacrylate, any derivative thereof, or a combination thereof.

In some embodiments, exposing the light polymerizable liquid to a first exposure of light characterized by a first region generates a first polymer in a first polymer region. In certain embodiments, the first polymer region is characterized by greater than or equal to 50% incorporation of the first polymerizable component. In some embodiments, a second exposure of light characterized by a second region generates a second polymer in a second polymer region. In preferred embodiments, the first polymer region and the second polymer region are different. In some embodiments, the second polymer region is characterized by greater than or equal to 50% incorporation of the second polymerizable component. In preferred embodiments the second region is adjacent to, contacting, or overlapping with, the first region.

In some embodiments, there are regional changes in the polymer composition, in contrast to what the polymer composition would be under bulk cure conditions. As a non-limiting example, a region of a resin may be irradiated with a source of radiation, wherein the resin comprises Monomer A and Monomer B. If the two monomers are capable of copolymerizing, then the composition of the copolymer that is formed would tend to average the input percentage (for example, 50% Monomer A and 50% Monomer B). However, using the techniques of this disclosure, the polymer composition can be altered in a three-dimensional X, Y, and Z region to be enriched in one of the two monomers, or the polymers the monomers form upon polymerization. For example, a planar X, Y-dimension with a vertical Z-plane may comprise 60% Polymer A and 40% Polymer B at a low value of the Z-plane, while a high value of the Z-plane may comprise 40% Polymer A and 60% Polymer B. In a second example, a resin initially comprising 60% Monomer A and 40% Monomer B may undergo controlled irradiation, thereby forming a region comprising 70% Monomer A and 30% Monomer B. In general, this disclosure provides a way to alter the polymer or copolymer composition in a defined X,Y region (and 3 dimensional X,Y,Z-space) to have a different composition than would be found under bulk polymerization. In some embodiments, the polymer composition in the irradiated region may comprise from 5% to 95% Polymer A and from 5% to 95% Polymer B. In certain embodiments, the polymer composition in the irradiated region may comprise from 50% to 100% Polymer A and from 0% to 50% Polymer B. In some embodiments, the polymer composition in the irradiated region may comprise from 1% to 100% Polymer A and from 0% to 99% Polymer B.

In some embodiments, the polymer formed in the first exposure region is characterized by one or more polymer properties that differ from the polymer formed in the second region. In certain embodiments, the first polymer and the second polymer differ from one another in Tg (glass transition temperature), storage modulus, elongation to break, or any combination thereof. In certain embodiments, the first polymer is characterized by a Tg that is at least 5° C. greater than the second polymer, at least 10° C. greater than the second polymer, at least 20° C. greater than the second polymer, at least 30° C. greater than the second polymer, at least 50° C. greater than the second polymer, at least 75° C. greater than the second polymer, or at least 100° C. greater than the second polymer. In some embodiments, the first polymer is characterized by a Tg that is from 1° C. to 5° C. greater than the second polymer, from 1° C. to 10° C. greater than the second polymer, from 1° C. to 20° C. greater than the second polymer, from 1° C. to 30° C. greater than the second polymer, from 1° C. to 50° C. greater than the second polymer, from 1° C. to 75° C. greater than the second polymer, from 1° C. to 100° C. greater than the second polymer, from 5° C. to 500° C. greater than the second polymer, from 10° C. to 1000° C. greater than the second polymer, from 20° C. to 200° C. greater than the second polymer, from 30° C. to 300° C. greater than the second polymer, from 50° C. to 500° C. greater than the second polymer, from 75° C. to 1000° C. greater than the second polymer, or from 100° C. to 1000° C. greater than the second polymer. In alternative embodiments, any of the above relationships can be reversed, that is, the second polymer can have a greater Tg than the first polymer characterized by any of the ranges disclosed above. More generally, each of the above ranges can characterize a difference between the values if Tg of the first and second polymer. Thus, the two polymers' glass transition temperatures can differ by at least 5° C., at least 10° C., at least 20° C., at least 30° C., at least 50° C., at least 75° C., or at least 100° C.; or they can differ by an amount from 1° C. to 5° C., 1° C. to 10° C., 1° C. to 20° C., 1° C. to 30° C., 1° C. to 50° C., 1° C. to 75° C., 1° C. to 100° C., 5° C. to 500° C., 10° C. to 1000° C., 20° C. to 200° C., 50° C. to 500° C., 75° C. to 1000° C., or 100° C. to 1000° C.

In some embodiments, the first polymer is characterized by a storage modulus that is at least 10 MPa greater than the second polymer, at least 20 MPa greater than the second polymer, at least 50 MPa greater than the second polymer, at least 100 MPa greater than the second polymer, at least 200 MPa greater than the second polymer, at least 300 MPa greater than the second polymer, at least 400 MPa greater than the second polymer, at least 500 MPa greater than the second polymer, at least 10 MPa less than the second polymer, at least 20 MPa less than the second polymer, at least 50 MPa less than the second polymer, at least 100 MPa less than the second polymer, at least 200 MPa less than the second polymer, at least 300 MPa less than the second polymer, at least 400 MPa less than the second polymer, or at least 500 MPa less than the second polymer.

In some embodiments, a fracture strain or an elongation to break is the ratio between the change in length and the initial length after breakage of a composition. In certain embodiments, the fracture strain provides a measure of the capacity of the composition to be deformed using an external force. In certain embodiments, a first polymer is characterized by an elongation to break that is differs from the elongation to break of a second polymer by more than 2%, by more than 5%, by more than 10%, by more than 15%, by more than 25%, by more than 30%, by more than 40%, by more than 50%, by more than 60%, by more than 70%, by more than 80%, by more than 90%, or by more than 95%.

In some embodiments, the composite material has greater than 30% transparency, greater than 40% transparency, greater than 50% transparency, greater than 60% transparency, greater than 70% transparency, greater than 80% transparency, greater than 90% transparency, or greater than 95% transparency. In preferred embodiments, the composite material has greater than 80% transparency.

In some embodiments, stress relaxation can be measured by monitoring the time-dependent stress resulting from a steady strain. The extent of stress relaxation can also depend on the temperature and moisture.

The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is m$^2$/s. Devices for measuring viscosity include viscometers and rheometers.

Composite Layers from a Single Resin

Figure 2:
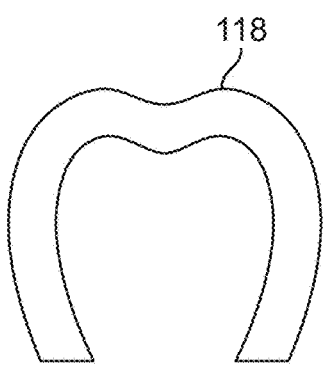
FIG. 2 depicts the cross-section of the dental appliance from FIG. 1.

In certain embodiments, the composite material can be used to create appliances. As a non-limiting example, a dental appliance can be created using the composite materials disclosed herein. FIG. 1 illustrates an exemplary orthodontic appliance 106 and jaw 104 including a patient's teeth. FIG. 2 illustrates orthodontic appliance cross-section 118 as taken along line 1C-1C of FIG. 1. The orthodontic appliance 106 may be designed to fit over a number of teeth present in an upper or lower jaw. An exemplary orthodontic device may be manufactured as disclosed by the methods discussed herein. As illustrated, the orthodontic appliance has a U-shaped cross-section to form one or more cavities for placement of a patient's teeth therein. The methods provided herein may be used to print the dental appliance, thus affording it high modulus strength and low elasticity. For example, techniques disclosed herein may be used to manufacture orthodontic appliances similar to those presented in US Patent Application Publication 2015/0004553, the disclosure of which is incorporated herein by reference in its entirety A composite material having a high modulus and low elasticity can generate the force needed to move teeth, while a composite material having a low modulus and high elasticity material to give the composite material both good mouth feel and low breakage. Finding a single material that has both of these properties is very difficult, and using a 3D printable resin with these two contrasting capabilities has not been possible to date. In certain embodiments, a stereolithographic 3D printer is used to obtain a material that behaves like a composite material by using reactivity differences of two or more different monomers, which then leads to 3D-spatially controlled compositional differences.

Mechanical properties of a material or structure of the appliance (e.g., stiffness, elongation, tensile strength, compressive strength, bending properties, viscoelastic properties, etc.) may be anisotropic, such that the properties are different when measured along x, y, and z directions. By changing the directionality of the structures, materials of an appliance, and/or source of radiation, varying properties can be developed along different directions (e.g., mesial-distal direction, occlusal-gingival direction, buccal-lingual direction, anterior-posterior direction, interior-exterior direction). Such variations in directionality can be achieved using the direct fabrication methods described herein, such as 3D printing.

In some embodiments, appliances with variable localized properties are presented herein and are produced by direct fabrication. The direct fabrication techniques presented herein may be particularly suited for manufacturing of appliances with different localized properties that would otherwise be difficult to achieve with other fabrication methods (e.g., indirect fabrication methods such as thermoforming a material sheet over a mold). For instance, in some embodiments, the direct fabrication techniques herein are used to fabricate appliances exhibiting variable thicknesses, variable stiffnesses, and/or variable material compositions at different portions of the appliance. For example, variable material compositions can be varied monomer component concentration present in printed appliance, wherein the composite is formed from a single resin. Additional description of direct fabrication methods suitable for producing the appliances of the present disclosure are provided further herein.

In some embodiments, the manufacture of a composite material derived from a single resin comprises single Vat, digital light processing (DLP), stereolithographic 3D printing, photocured material jetting, photocured fused deposition modeling (FDM), a hybrid thereof, or a combination thereof. In certain embodiments, the process uses light intensity to direct where one material of the composite forms relative to a second material in the composite. In some embodiments, the process of using light intensity to direct the formation of material in the composition also allows for the creation of different patterns of tensile strength and modulus within the material, such as an orthodontic appliance. In some embodiments, the process directs compositional differences in both vertical and horizontal dimensions. In certain embodiments, the composite material disclosed herein could be made from a standard thermoplastic composite. The process may direct phase separation in both vertical and horizontal dimensions.

Common current orthodontic appliance materials include composites that use a high modulus (low elongation) material sandwiched between two high elongation (low modulus) materials. This configuration allows the overall material to provide enough force (from the high modulus material) to move teeth, but does not break when inserting or removing (from the high elongation material).

Attempts to create a material with these characteristics (high modulus and high elongation) in a homogenous material have been less than ideal in at least some aspects. Creating homogenous materials is difficult due to stress relaxation in high humidity environments. The traditional approach is to use hydrogen bonding to obtain a tough material (high modulus and high elongation), however, in moist environments, hydrogen bonded materials lose their toughness and will show increased stress relaxation. Attempts to create a 3D printable resin that is tough have also used hydrogen bonding; and consequently have provided similar high stress relaxation.

Thus, it is desirable to create a composite structure on a 3D printer to obtain a tough material that does not require hydrogen bonding. The material may include hydrogen bonding if desired. In some embodiments, the composite material is obtained by first choosing at least two different types of monomers components that have different reactivities. In a non-limiting example, Monomer 1 prefers to react with itself more than with Monomer 2, but Monomer 2 also reacts preferentially with Monomer 1. Additionally, Monomer 1 and Monomer 2 are able to polymerize with a reasonable rate to make them applicable for 3D printing. The resulting mixture is more likely to polymerize Monomer 1 when exposed to conditions which promote polymerization, such as exposure to light and a photoinitiator.

In some embodiments, Monomer 1 and Monomer 2 comprise more than one type of monomer. As a non-limiting example, monomer 1 can be a methacrylate and monomer 2 can be a mixture of thiol and allyl ether components. In this example, the methacrylate tends to react first, then the thiol-ene (the allyl ether and thiol) will copolymerize. Photoinitiators and thermal initiators, or other forms of catalysts or reactive species may be used separately or combined to initiate polymerization of monomer 1 and/or monomer 2.

In some embodiments, the monomers are monofunctional. In certain embodiments, the monomers have a plurality of functionalities. In certain embodiments, the monomers are difunctional. In some embodiments, the monomers are trifunctional.

In another embodiment, monomer 1 is an acrylate and monomer 2 is a methacrylate. The two monomers are mixed and a photoinitiator is added. The resin is then placed in a vat of a top down 3D printer. The choice for any given layer is a single exposure to create a homogenous material or multiple exposures per layer to create a composite material in that layer.

In some embodiments, the photoinitiation of the polymerization reaction uses a mask or other mechanism for forming a patterned light shield for a portion of the polymerizable resin comprising monomer 1 and monomer 2. While the mask is present, an exposure of light will cause the monomer 1 to preferentially polymerize in the exposed areas. During and after the exposure, monomer 1 from areas directly adjacent to the exposed area will diffuse into the exposed area and react as long as radicals or other reactive species or catalysts are still present or are being generated. Monomer 2 will be diluted by this process and in some cases even diffuse counter to monomer 1. The result is that the first exposure generates a polymer that is has a higher incorporation of monomer 1 than of monomer 2. A second exposure can then be applied. The second exposure may be to the entire polymerizable solution, to a different masked area (with or without overlap of the first masked area) or may use a different condition to induce polymerization, such as using heat to induce thermal polymerization. In the second exposure, some regions will have a higher concentration of monomer 2 than the starting resin due to the diffusion caused by the first exposure, and the polymer that forms in those regions will have a greater incorporation of monomer 2. Accordingly, a single layer may have regions of polymer composed mostly of monomer 1, and regions of polymer composed mostly of monomer 2. In some embodiments, the resulting polymer composition comprises an even mix of monomer 1 and monomer 2, which may occur if the regions are too distant form the first exposed region for diffusion to affect the monomer concentrations. For example, resins using more than two monomers can allow for creation of regions in the layer that differ in concentration for all monomers added to the resin formulation and polymerized into a composite material.

Manufacturing Techniques and Applications

Figure 6:
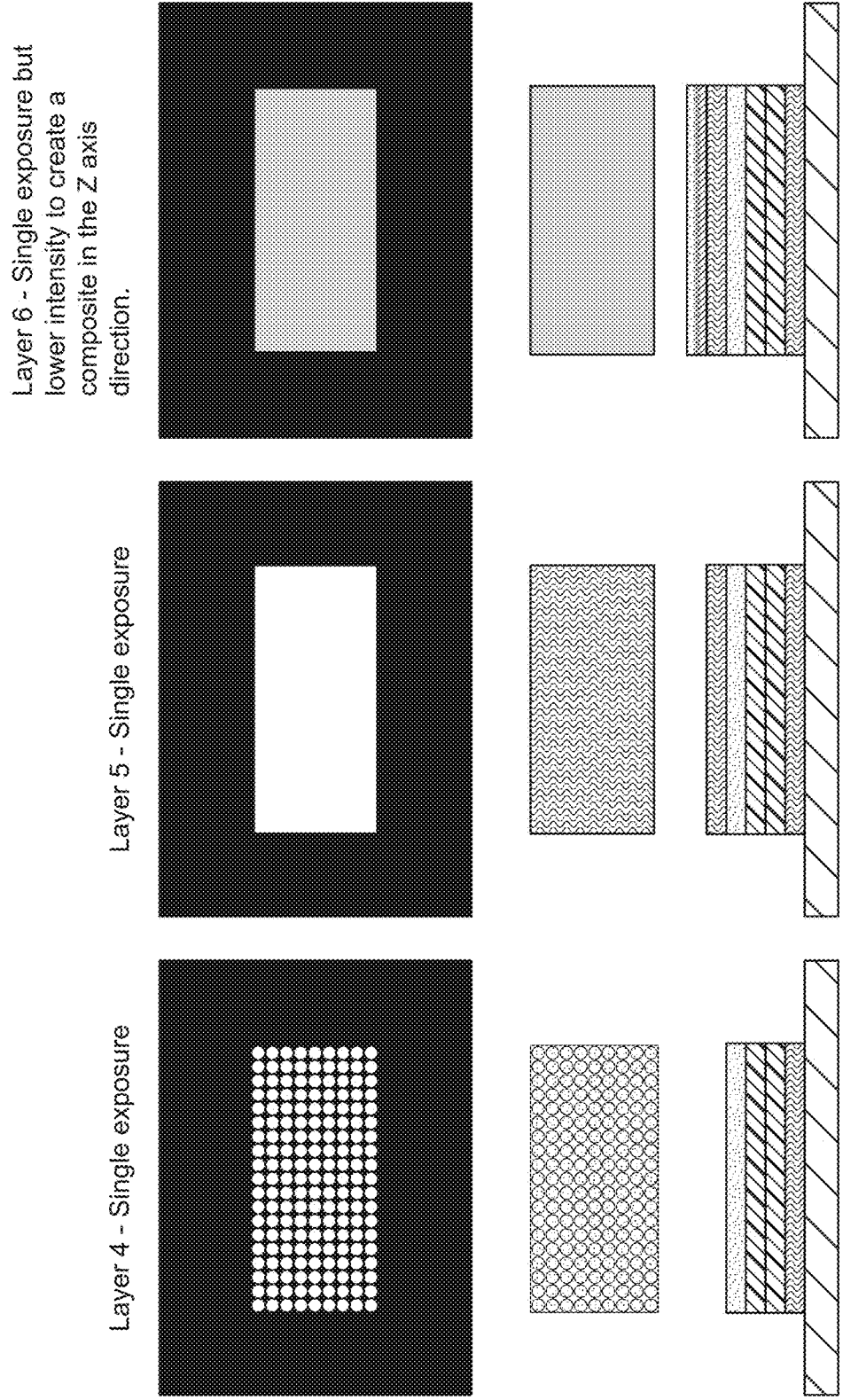
FIG. 6 depicts the formation of blayers 4, 5, and 6 of a composite material, including the use of a lower light intensity to create the sixth layer, resulting in the formation of a gradient in the Z-axis.
Figure 7:
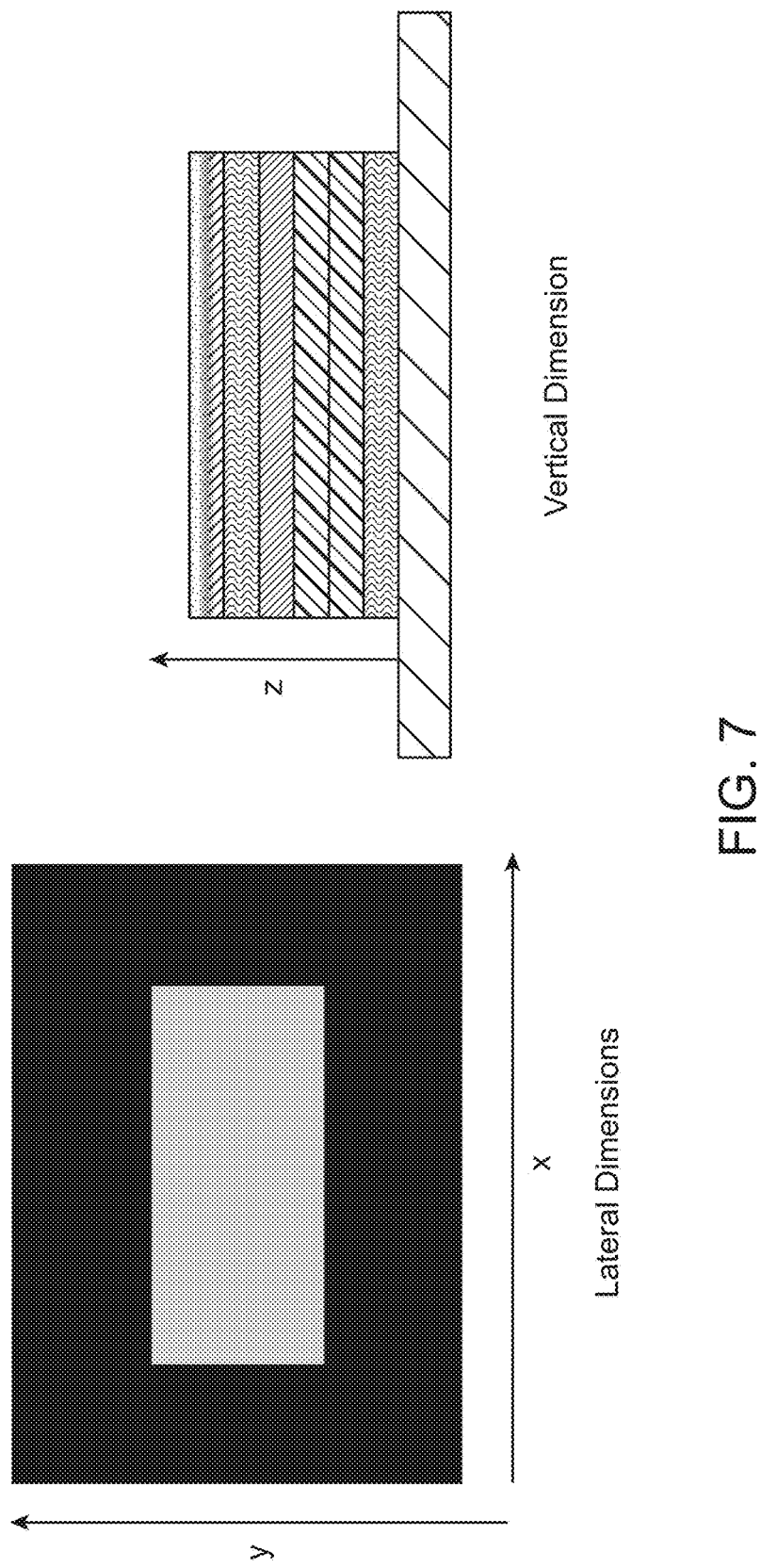
FIG. 7 depicts the lateral dimensions and vertical dimension as used herein.

In certain embodiments, a composite may be created having a plurality of layers, wherein different layers within the plurality have different properties (FIG. 3). In an exemplary embodiment, a build platform is obtained having a print area as depicted in FIG. 4. A homogenous resin comprising equal parts of monomer 1 and monomer 2 is positioned on the build platform, and is then exposed to an unmasked source of radiation, thus initiating polymerization to form a copolymer without diffusion (FIG. 4, central panel). This first layer polymer is composed equally of monomer 1 and monomer 2. A second layer of the resin is positioned on top of the first layer, and monomer 1 is preferentially polymerized by the source of radiation in a plurality of regions, with the aid of a masking pattern (FIG. 4, right panel). The resulting composite material 1 has a polymer composed of a majority of monomer 1. Due to diffusion, the regions not exposed to the source of radiation are comprised mostly of monomer 2. A second exposure of the second layer uses a masking pattern that is the opposite of the first pattern used (FIG. 5, left panel), and is exposed to the source of radiation to form a second polymer incorporating mostly monomer 2. Accordingly, the second layer contains a composite material comprising a polymer mostly composed of monomer 1 and a second polymer mostly composed of monomer 2. A third layer is positioned on top of the second layer (FIG. 5, central panel), and monomer 1 is preferentially polymerized by the source of radiation in a plurality of regions, with the aid of a masking pattern. Due to diffusion, the majority of monomer 2 moves to regions that have not yet been exposed to the source of radiation. Following removal of the masking device, the entire platform is exposed to the source of radiation, resulting in the polymerization of monomer 2 into a polymer comprising of mostly monomer 2 (FIG. 5, right panel). The following exposure is a blanket exposure and cures all the areas previously exposed in addition to areas not exposed. The areas next to the previously exposed regions will contain a higher concentration of monomer 2 and will thus form a polymer preferentially incorporating monomer 2. Accordingly, the third layer contains a composite material comprising a polymer mostly composed of monomer 1 and a second polymer mostly composed of monomer 2. A fourth layer is positioned on top of the third layer (FIG. 6, left panel), and monomer 1 is preferentially polymerized by the source of radiation in a plurality of regions, with the aid of a masking pattern. The unpolymerized monomer can either be drained, polymerized by other means such as thermal treatment, or left inside the layer as liquid pockets. Later treatments can infuse a new material if desired. A fifth layer of resin is positioned on top of the fourth layer (FIG. 6, center panel), and the entire platform is exposed, thus forming a polymer comprising nearly equal portions of monomer 1 and monomer 2. Finally, a sixth layer of resin is positioned on top of the fifth layer (FIG. 6, right panel). A low intensity radiation is used to preferentially polymerize monomer 1 near the top of the layer. Diffusion of monomers 1 and 2 results in a gradient formation. Accordingly, layer 6 comprises polymers having a majority of monomer 1 near the top of the Z-axis, and polymers having a majority of monomer 2 near the bottom of the Z-axis (FIG. 6, right panel, FIG. 7). The exposure is dimmed in comparison to the exposures used for the other layers causing preferential polymerization to occur at the surface (in the direction of the light) and diffusion to occur away from the surface.

For any given layer, one or a plurality of exposures can be used. Each exposure can be slow or fast, and can be of variable intensities for each exposure. In certain embodiments, top down or bottom up 3D printers that use light to polymerize resin can be used. In certain embodiments, the methods herein use printers, such as the AutoDesk Ember, the Gizmo 3D printer, Octave printers, Full Spectrum Laser 3D printers, Inkjet 3D printers, stereolithographic 3D printers, and the like. Inkjet 3D printers are capable of creating composite materials but are generally limited on the resolution that is obtained compared to stereolithographic type of 3D printers.

In certain embodiments, monomer 1 and monomer 2 are partially miscible with each other. In preferred embodiments, monomer 1 and monomer 2 are fully miscible with each other. In some embodiments, monomer 2 is partially or fully immiscible in polymer 1, wherein polymer 1 is a polymer formed from a majority of monomer 1. Counter diffusion of monomer 2 is enhanced if monomer 2 is partially or fully immiscible in Polymer 1. In some embodiments, it is desirable to have a first exposure for a layer to form a polymer primarily composed of monomer 1 and then move to the next layer, thus leaving only a structure composed primarily of polymer of monomer 1. In some embodiments, it is desirable to vary the composition of formed polymer in the z dimension in addition to or independent of the x and y dimensions by using the methods taught in U.S. Pat. No. 8,921,447, which is hereby incorporated by reference.

In some embodiments, processes described herein may be influenced by a first region created from a first polymer comprising a majority of monomer 1. In some embodiments the first region is influenced by both the wavelength of light and by the diffusion rates of the monomers. In certain embodiments, the lower bound for the smallest dimension of the composite structures is governed by the light source. As a non-limiting example, when using a laser, the width of a laser beam at its focus can achieve dimension sizes of 10s of nanometers to microns. Smaller dimension sizes are achievable in some embodiments wherein two photon techniques or holography is used. In some embodiments digital light processing (DLP) projectors are used, and they can be limited by the inherent resolution of the projectors, which typically give X-Y resolutions of greater than 20 microns. In more typical embodiments, DLP projectors give X-Y resolutions of greater than 50 microns. In some embodiments, the diffusion rate of either monomer 1, monomer 2, the light intensity, the temperature, or a combination thereof govern the upper bound in the smallest obtainable dimensional size of the composite structures. Factors that influence the diffusion rate include temperature, size of the monomers, viscosity, shape of the monomers, and other molecular factors. Fast diffusion corresponds with the ability to create larger structures in a reasonable amount of time. In preferred embodiments, structure sizes range from 10's of nanometers to 500 microns in the X-Y dimensions. In certain embodiments, the Z dimension is governed by the motor and drive mechanism used to move the build platform and typically is larger than 1 micron. In some embodiments, the Z dimension is greater than 10 nm, greater than 20 nm, greater than 30 nm, greater than 50 nm, greater than 100 nm, greater than 200 nm, greater than 250 nm, greater than 500 nm, greater than 750 nm, greater than 1 micron, greater than 2 microns, greater than 3 microns, greater than 4 microns, greater than 5 microns, greater than 10 microns, greater than 20 microns, greater than 30 microns, greater than 50 microns, greater than 75 microns, greater than 100 microns, greater than 200 microns, greater than 300 microns, greater than 500 microns, greater than 750 microns, or greater than 1 mm. In some embodiments, the Z dimension is from 0.01 nm to 10 nm, from 0.1 nm to 10 nm, from 0.5 nm to 10 nm, from 0.1 nm to 1 nm, from 1 nm to 10 nm, from 1 nm to 20 nm, from 1 nm to 30 nm, from 1 nm to 50 nm, from 1 nm to 100 nm, from 1 nm to 200 nm, from 1 nm to 250 nm, from 1 nm to 500 nm, from 1 nm to 750 nm, from 1 nm to 1 micron, from 1 nm to 2 microns, from 1 nm to 3 microns, from 1 nm to 4 microns, from 1 nm to 5 microns, from 1 nm to 10 microns, from 1 nm to 20 microns, from 1 nm to 30 microns, from 1 nm to 50 microns, from 1 nm to 75 microns, from 1 nm to 100 microns, from 1 nm to 200 microns, from 1 nm to 300 microns, from 1 nm to 500 microns, from 1 nm to 750 microns, or from 1 nm to 1 mm.

In certain embodiments, a holographic pattern is used to create light and dark regions during exposure to the source of radiation. In preferred embodiments, a holographic projector is utilized to activate holograms for 3D printing. With advanced calculations, an object can be printed using a holographic image of the object in a volume of liquid without the need for printing layers. In addition, since holographic images are interference patterns, they are already composed of light and dark regions on a nanometer scale. Since diffusion is faster on small spatial scales, the intensity of the light can be higher and the layer is created faster than if larger light and dark regions are used.

In some embodiments, the processes disclosed herein create a material with a planar composite structure with alternating layers of high modulus and high elongation materials, including composite structures useful in orthodontic appliances. Additionally, the tensile or compressional force can be adjusted in different regions of the orthodontic appliance as desired.

Outside of the orthodontic field, other applications may benefit from the processes and techniques described herein. Having the ability to create a composite material that is spatially defined out of a single resin is a large step forward and opens the possibility of 3D circuits including the use of conductive and nonconductive materials, data storage, structural materials, shape changing materials, spatially controlled ceramics, and a whole host of other uses.

In some embodiments, the present disclosure describes applications that may be applied to aerospace engineering. A composite material may be formed from a single resin comprising materials that are advantageous to use in aerospace applications. As a non-limiting example, a composite material comprising monomer or polymer compositions and further comprising ceramics may provide increased strength modulus. Composite materials can be beneficial to aerospace applications, such as electromagnetic shielding, provide improved tribological properties, and providing improved coatings. In some embodiments, the resulting composite material provides a lightweight alternative to conventional materials. In certain embodiments, the production of the composite material provides an affordable alternative to conventional materials. In certain embodiments, a resin comprising monomer components can further comprise a clay. In some embodiments, a resin comprising a clay or ceramic can undergo polymerization to form a polymer matrix embedded with the clay or ceramic. In certain embodiments, the resin comprises ceramic nanocomposites, and the resulting composite material also comprises ceramic nanocomposites.

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of this disclosure. Thus, it should be understood that although the present disclsoure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended claims. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, of the group members, are disclosed separately. When a Markush group or other grouping is used herein, all individual members of the group and all combinations and subcombinations possible of the group are intended to be individually included in the disclosure. When a compound is described herein such that a particular isomer, for example, in a formula or in a chemical name, that description is intended to include each isomers a of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods and materials are now described. Nothing herein is to be construed as an admission that the invention is not entitled to antedate such disclosure by virtue of prior invention.

Every formulation or combination of components described or exemplified herein can be used to practice this disclosure, unless otherwise stated.

Whenever a range is given in the specification, for example, a temperature range, a pressure range, a modulus range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of this disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of this disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

While preferred embodiments of the present disclosure have been shown and described herein, it is to be understood that the disclosure is not limited to the particular embodiments of the disclosure described below, as variations of the particular embodiments are made and still fall within the scope of the appended claims. It is also to be understood that the terminology employed is for the purpose of describing particular embodiments of the disclosure, and is not intended to be limiting. Instead, the scope of the present disclosure is established by the appended claims. In this specification and the appended claims, the singular forms "a," "an" and "the" include plural reference unless the context clearly dictates otherwise.

The particulars shown herein are by way of example and for purposes of illustrative discussion of the preferred embodiments of the present disclosure only and are presented in the cause of providing what is believed to be the most useful and readily understood description of the principles and conceptual embodiments of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure are embodied in practice.

EXAMPLES

The following examples are put forth so as to provide those of ordinary skill in the art with a complete disclosure and description of how to make and use the present disclosure and are not intended to limit the scope of what is regarded as the disclosure nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Composite Layer Comprising Dogbone Pattern

This Example describes a method of creating a composite material, wherein a dogbone shaped pattern is used to create regions of polymerization in the resultant composition. A dogbone pattern comprises two large shoulders and a gage section in between (see FIG. 9A). A comparison is made between full exposure of each dogbone-shaped region with the use of a mask to create a plurality of lines.

A resin was created by mixing tricyclodecane diacrylate (1 gram), isobornyl acrylate (3 grams), Exothane 8 (4 grams), Irgacure 819 (0.096 gram), and AIBN (0.088 gram). The resin was mixed vigorously until all reagents were fully dissolved.

A portion of the resin was placed between two glass slides with a 500-micrometer spacer, thereby forming a 500-micrometer layer of resin ("Sample 1"). Using the resin, this step was repeated in order to form Sample 2 and Sample 3.

Figure 9B:
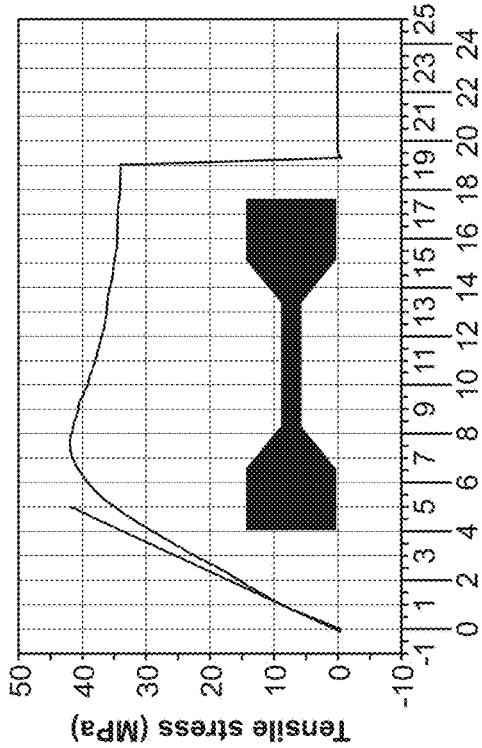
FIG. 9B depicts results of a tensile test wherein the composition is homogenous.
Figure 9D:
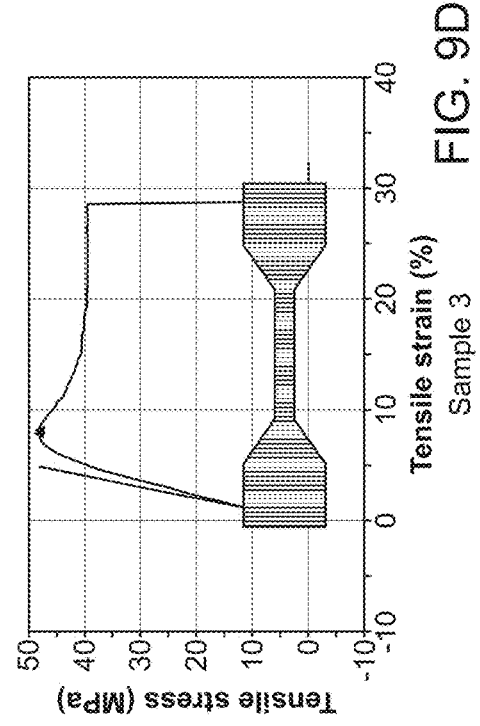
FIG. 9D depicts results of a tensile test wherein the composition comprises selectively polymerized lines perpendicular to the long axis of the dogbone component.
Figure 9A:
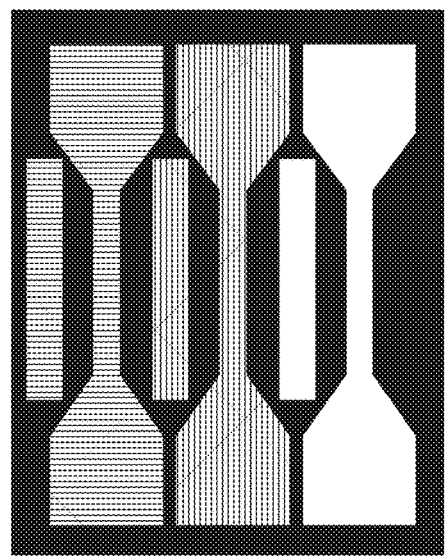
FIG. 9A depicts dogbone patterning for creating a masked exposure.

A dogbone pattern was projected onto the samples, as depicted in FIG. 9A. Sample 1 was masked using a plain dogbone pattern (FIG. 9A, bottom). Sample 2 was masked using a dogbone pattern having lines that were parallel to the long axis of the dogbone (FIG. 9A, center). Sample 3 was masked using a dogbone pattern having lines that were perpendicular to the long axis of the dogbone (FIG. 9A, top). Each sample was cured using an Acer H6510BD DLP projector (Model H1P1117) light for 5 minutes. The samples were then exposed for a second time using just the blank dogbone (no pattern), curing any uncured regions from the first exposure. Then the excess uncured liquid was poured out of the slides and all three samples were heated to 100° C. for 15 minutes. The samples were then removed from the glass slide sandwich and cleaned with isopropanol, dried, and allowed to sit 24 hours before testing.

The composite materials were each tested and characterized (Table 1).

TABLE 1

Comparison of dogbone patterning and dogbone patterning with stripes

| Characterization | Sample 1 | Sample 2 | Sample 3 |
|---|---|---|---|
| Young's modulus | 830 MPa | 850 MPa | 997 MPa |
| Transition temperature Tg | 90° C. | 88° C. | 92° C. |
| Elongation to yield | 7% | 8% | 8% |
| Elongation to break | 19% | 40% | 32% |
| Storage modulus | 1700 MPa | 1800 MPa | 2100 MPa |
| Storage modulus at 70° C. | 526 MPa | 490 MPa | 570 MPa |

Figure 9C:
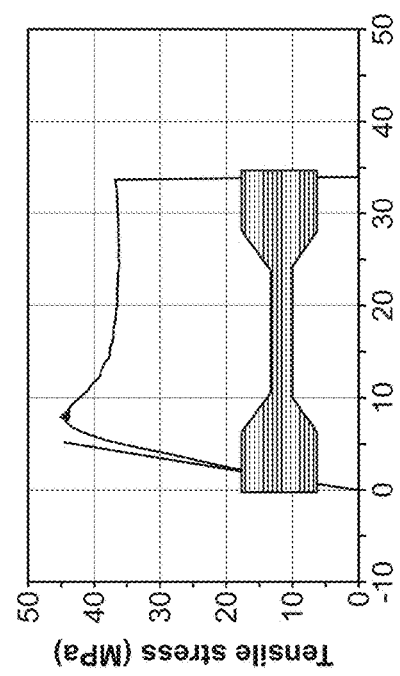
FIG. 9C depicts results of a tensile test wherein the composition comprises selectively polymerized lines parallel to the long axis of the dogbone component.

The material in Sample 1 was a homogenous polymer material composed of both monomer 1 and monomer 2, and is an example of localized bulk cure. In Sample 2, a composite material with alternating lines of polymer comprised mostly of the methacrylate polymer was formed, running parallel to the long axis of the dogbone due to the exposure region provided by the mask. The elongation to break character of Sample 2 was more than double that of Sample 1 (see: FIG. 9B, FIG. 9C). Sample 3 was also a composite material with alternating lines of polymer comprised mostly of the methacrylate polymer, but the lines ran perpendicular to the long axis of the dogbone due to the exposure region provided by the mask. The elongation to break character of Sample 3 was higher than that of Sample 1, but less than Sample 2 (FIG. 9D). This result shows that the direction of exposure patterning can play an important role in the resulting composite materials.

Example 2

Composite Layer Comprising Dogbone Pattern Mask

This Example describes a method of creating a composite material, wherein a vertical patterning material is used to increase elongation when compared to the bulk cured material.

A resin comprising a hard phase (31 wt. % isobornyl methacrylate and 10.7 wt. % bisphenol A dimethacrylate), a semi-hard phase that ties the two monomer systems together (17.9 wt. % tert-butylacrylate), a soft hard phase (31.9 wt. % vinyl propionate and 5.1 wt. % vinyl laurate), and an initiator system (2.1 wt. % TPO-L and 1% AIBN) was mixed until all reagents were fully resolved.

A portion of the resin was placed between two glass slides with a 500-micrometer spacer, thereby forming a 500-micrometer layer of resin. A first layer of resin was cured with a 50-micrometer grating pattern. A second layer of resin was formed in the same manner, and was cured without a micrometer grating pattern. The layers were cured using 1 mW light at 400 nm for 10 minutes. The pattern was removed, and both samples were further cured with irradiation for an additional 5 minutes at 50 mW, then heated to 100° C. for 1 hour.

The fully exposed film was removed from the glass slides, and dog bone shapes were cut from the material to test on a tensile tester. The bulk polymer material without patterned exposure comprised a homogenous mixture of components, and had a Young's modulus of 1500 MPa, and an elongation to yield of 3%.

In comparison, the polymer material with patterned exposure comprised 50-micron wide regions rich in methacrylate, because the methacrylate cured first to form a copolymer with the acrylate. The pattern alternated with 50-micron wide regions rich in vinyl ester, because the vinyl ester tended to cure last to form a copolymer with the acrylate. Dog bone shapes were cut from the material to test on a tensile tester. The patterned exposure had a Young's modulus of 1400 MPa, and an elongation to yield of 8%.

Example 3

Cationic Curing System

This Example describes a method of curing a polymer composite material using cationic curing.

A resin comprising a hard phase (48.7 wt. % Omnilane OC 1005, an epoxide), a soft phase (49.6 wt. % isobutyl vinyl ether), and a cationic initiator system (1 wt. % iodonium salt, 0.7 wt. % 9-vinyl carbazole) was mixed until all reagents were fully dissolved.

A portion of the resin was placed between two glass slides with a 500-micrometer spacer, thereby forming a 500-micrometer layer of resin. A first layer of resin was cured with a 50-micrometer grating pattern. A second layer of resin was formed in the same manner, and was cured without a micrometer grating pattern. The layers were cured using 1 mW light at 380 nm for 10 minutes. The pattern was removed, and both samples were further cured with irradiation for an additional 5 minutes at 50 mW, then heated to 100° C. for 1 hour.

The fully exposed film was removed from the glass slides, and dog bone shapes were cut from the material to test on a tensile tester. The bulk material without patterned exposure had turned white due to phase separation between the polyvinyl ether and the epoxide monomer.

During the second light exposure, the dark areas of the patterned film were cured. If left alone, the dark areas will cure without the second light exposure due to cationic polymerization, which will be cured with diffusion by the reactive cation. As the spacing between the grating pattern decreased from 100 micrometers to 10 micrometers, samples became observably clearer, and were also easier to handle. Accordingly, small iterations of patterning throughout the system generated a more robust product.

Example 4

Formation of an Interpenetrating Network

This Example describes a method of forming an interpenetrating network. Interpenetrating networks typically allow for phase separation by separation of cure mechanisms.

A resin comprising an acrylate phase (39.5 wt. % tert-butyl acrylate, 5.9 wt. % isodecyl acrylate (Photomer 4810), 1.9 wt. % tricyclodecane diacrylate), an epoxy-anhydride phase (22 wt. % Omnilane 1005, 26 wt. % hexahydro-4-methylphthalic anhydride), a free radical photoinitiator (1.5 wt. % TPO-L), and a thermal epoxy-anhydride catalyst (3.2 wt. %) was mixed until all reagents were fully dissolved.

A portion of the resin was placed between two glass slides with a 500-micrometer spacer, thereby forming a 500-micrometer layer of resin. A first layer of resin was cured with a 50-micrometer grating pattern. A second layer of resin was formed in the same manner, and was cured without a micrometer grating pattern. The layers were cured using 1 mW light at 380 nm for 10 minutes. The pattern was removed, and both samples were further cured with irradiation for an additional 5 minutes at 50 mW, then heated to 100° C. for 1 hour. The second blanket-exposure ensured the acrylate was fully polymerized.

The fully exposed film was removed from the glass slides, and dog bone shapes were cut from the material to test on a tensile tester. The bulk material without patterned exposure had turned white due to phase separation between the polyacrylate and the epoxy-anhydride oligomers.

The patterned exposed film was removed from the glass slides, and had also turned white white. A comparison of patterns revealed that samples were less brittle as the pattern size decreased. All samples showed a microphase separation, even in areas undergoing initial irradiation. Accordingly, the epoxy-anhydride species did not have time to diffuse away from the irradiated regions before being trapped in the acrylate mix. A better separation of materials is possible using a smaller light pattern and/or a lower light intensity with more crosslinking of the acrylate.

Example 5

Comparison of Masked and Non-Masked Patterned Light

This Example describes a method of forming different polymer composite materials using patterned masked and direct pattern light.

A resin comprising a vinyl ester phase (35 wt. % vinyl tert-butyl benzoate, 15 wt. % divinyl adipate), an acrylate phase (40 wt. % tert-butyl acrylate, 8.75 wt. % isodecyl acrylate), and initiators (2 wt. % TPO-L, 0.25 wt. % AIBN) was mixed until all reagents were fully dissolved.

A portion of the resin was placed between two glass slides with a 500-micrometer spacer, thereby forming a 500-micrometer layer of resin. A first layer of resin was cured with a 50_10 mask pattern, whereby 5 micrometers of light and 10 micrometers of dark were used as the masking pattern. The layer was cured using 0.2 mW light at 365 nm for 10 minutes. The mask pattern was then removed and the layer was irradiated an additional 5 minutes at 1 mW at 100° C. The first layer was then heated to 100° C. for an additional hour. The first layer was removed from the glass slide and dog bones were cut from the material to test on a tensile tester.

A second layer of resin was formed in the same manner, and was patterned directly using a light source (i.e., no patterning mask was used). The interference pattern was generated from a 405 nm laser and a Lyod's mirror arrangement set at a 5-micrometer interference pattern. The second layer was cured with the patterned light at 0.2 mW and 365 nm for 10 minutes. The full layer was then irradiated for 5 minutes at 1 mW at 100° C. The second layer was then heated to 100° C. for an additional hour. The second layer was removed from the glass slide and dog bones were cut from the material to test on a tensile tester.

A third layer of resin was formed in the same manner, and was exposed without pattern to a first light exposure using 0.2 mW at 365 nm for 10 minutes. The third layer was then further irradiated for 5 minutes at 1 mW at 100° C. The third layer was then heated to 100° C. for an additional hour. The third layer was removed from the glass slide and dog bones were cut from the material to test on a tensile tester.

The masked patterned exposure at the vertical pattern (parallel to the gauge length) had a Young's modulus of 1515 MPa, an elongation to yield of 25%, and a strength of 39 MPa. The direct pattern light using a laser pattern at the vertical pattern (parallel to the gauge length) had a Young's modulus of 1420 MPa, an elongation to yield of 20%, and a strength of 40 MPa. The material obtained by mixed bulk cure (third layer) had a Young's modulus of 1380 MPa, an elongation to yield of 16%, and a strength of 41 MPa.

Figure 8B:
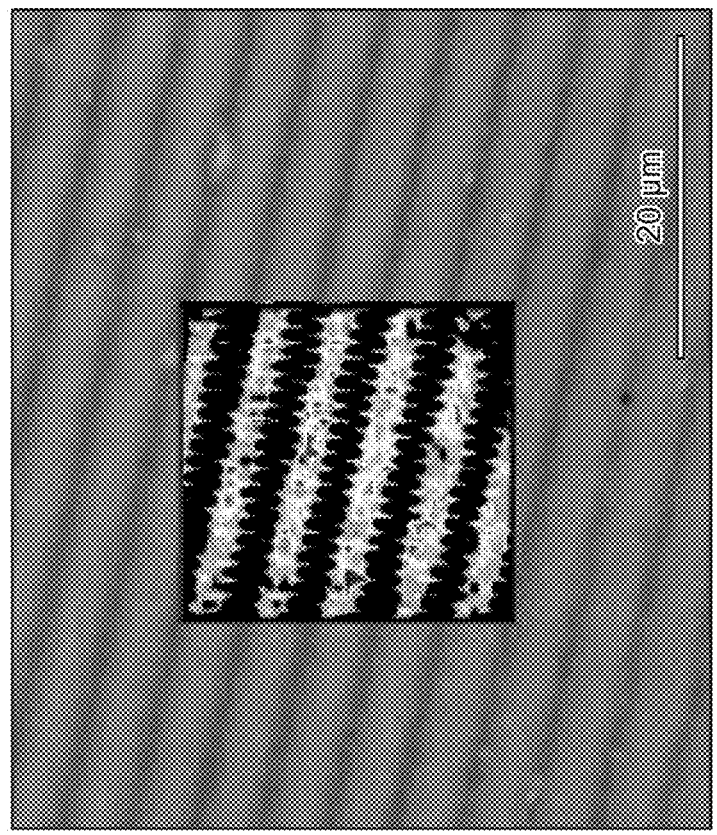
FIG. 8B depicts the optical image and inset Raman map of a sample irradiated using a direct interference pattern from a laser.

As can be seen with the optical images of each layer (FIG. 8A, FIG. 8B), both patterns produce a clear optical pattern that is created in the material from refractive index differences between the exposed and the dark regions. The inset Raman heat maps indicate about a 10% enrichment of acrylate in the first irradiated region, and about a 10% enrichment of the vinyl ester in what was the dark region in the first irradiation. The difference in spatial composition is sufficient to create a material with properties that are distinct from the material obtained by mixed bulk cure.

Figure 8A:
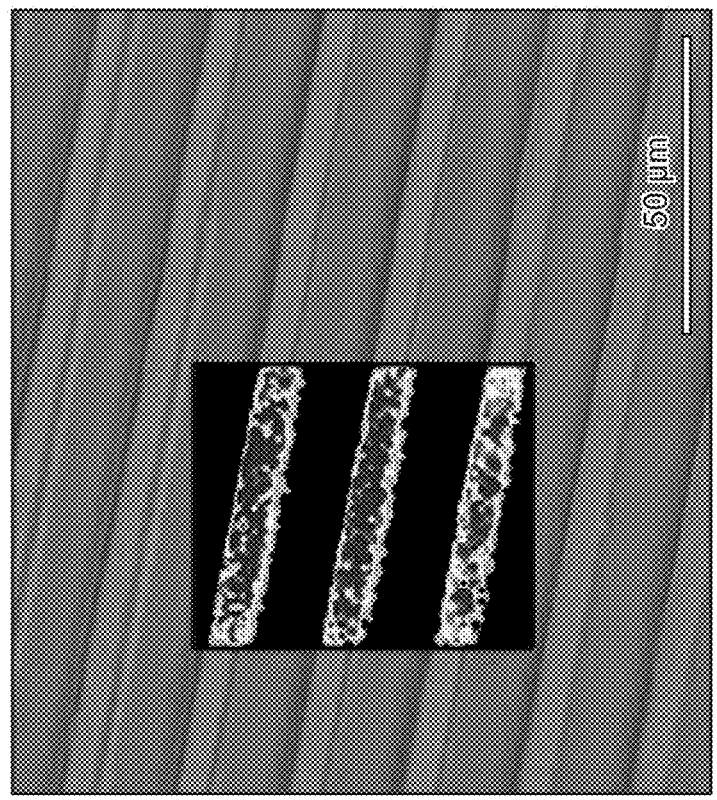
FIG. 8A depicts the optical image and inset Raman map of a sample irradiated using a 5_10 mask.

An optical image of the first layer (the masked pattern) is displayed in FIG. 8A, and the inset displays a Raman heat map of the sample. The lighter-colored bars display the thinner (approximately 5-micrometers thick) lines comprising an enriched population of acrylate, while the parallel darker bars display the thicker (approximately 10-micrometers thick) regions comprising an enriched population of the vinyl ester. Similarly, FIG. 8B displays an optical image of the second layer (the laser pattern), and the inset displays a Raman heat map of the sample. As above, the lighter-colored lines display an enriched population of acrylate, while the parallel darker bars display the regions comprising an enriched population of the vinyl ester.

What is claimed is:

1. A method of making a composite polymer composition from a single resin, the process comprising:
   providing a resin, the resin comprising a first monomer component and a second monomer component, the resin characterized by a resin ratio of the first monomer component to the second monomer component;
   polymerizing the first monomer component by exposing the resin to a first exposure of light;
   forming a first region having a first ratio of the first monomer component to the second monomer component, wherein the first region has a vertical dimension between 50 µm and 250 µm; and
   forming a second region having a second ratio of the first monomer component to the second monomer component, wherein the resin ratio, the first ratio, and the second ratio are different.

2. The method of claim 1, further comprising polymerizing the second monomer component.

3. The method of claim 1, wherein the polymerizing the first monomer component comprises exposing the resin to a source of radiation.

4. The method of claim 3, wherein the source of radiation comprises ultraviolet light, visible light, infrared light, microwave irradiation, laser exposure, holography, DLP projection, optical lithography, pulsed light, or a combination thereof.

5. The method of claim 2, wherein the polymerizing the first monomer component forms a first polymer and wherein the polymerizing the second monomer component forms a second polymer.

6. The method of claim 2, wherein the polymerizing the second monomer component results in a polymerization-induced phase separation along one or more lateral directions.

7. The method of claim 5, wherein the first region and the second region are separated by a concentration gradient, wherein the concentration gradient comprises the concentrations of the first monomer component, the second monomer component, the first polymer, and the second polymer.

8. The method of claim 2, wherein:
   the polymerizing the first monomer component uses a source of radiation; and
   the polymerizing the second monomer component uses a secondary photopolymerization, wherein the secondary photopolymerization uses a second source of radiation, said second source of radiation comprising ultraviolet light, visible light, infrared light, microwave irradiation, or a combination thereof.

9. The method of claim 2, wherein:
   the polymerizing the first monomer component comprises using a source of radiation; and
   the polymerizing the second monomer component comprises using the same source of radiation.

10. The method of claim 1, wherein the first monomer component and the second monomer component are miscible.

11. The method of claim 5, wherein the second monomer component is immiscible in the first polymer.

12. The method of claim 1, wherein the first monomer component comprises one or more of a methacrylate monomer, an acrylate monomer, a thiol monomer, a vinyl acetate monomer, a styrene monomer, a vinyl ether monomer, a derivative thereof, or a combination thereof.

13. The method of claim 1, wherein the second monomer component comprises one or more of an acrylate monomer, a thiol monomer, an allyl ether monomer, a vinyl acetate monomer, a vinyl chloride monomer, an acrylonitrile monomer, a vinyl ether monomer, a vinyl silane monomer, a vinyl siloxane monomer, a butadiene monomer, a norbornene monomer, a maleate monomer, a fumarate monomer, an epoxide monomer, an anhydride monomer, a hydroxyl monomer, a derivative thereof, or a combination thereof.

14. The method of claim 1, wherein from 10 to 90 wt % of the resin consists of the first monomer component.

15. The method of claim 1, wherein from 10 to 90 wt % of the resin consists of the second monomer component.

16. The method of claim 1, wherein the first monomer component is from 5-fold to 1000-fold more reactive than the second monomer component.

17. The method of claim 1, wherein the first monomer component and the second monomer component have a difference in reactivity, wherein the difference in the reactivity of the first monomer component and the reactivity of the second monomer component comprises a difference in a polymerization rate coefficient, a difference in concentration, a difference in functionality, a difference in solubility, a difference in diffusivity of the first monomer component, a difference in diffusivity of the second monomer component, or any combination thereof.

18. The method of claim 1, wherein the first monomer component and the second monomer component have a difference in reactivity, wherein the difference in the reactivity of the first monomer component and the reactivity of the second monomer component comprises a difference in oxygen inhibition, a difference in light absorption, a difference in photoinitator concentration, or a combination thereof.

19. The method of claim 1, wherein the first region has at least one lateral dimension less than or equal to 100 µm.

20. The method of claim 1, wherein the second region has at least one lateral dimension less than or equal to 300 µm.

21. The method of claim 3, wherein the source of radiation initiates polymerization of the first monomer component in a first exposure region, wherein the first exposure region is exposed to a first light intensity of less than 20 mW/cm$^2$.

22. The method of claim 21, wherein the source of radiation initiates polymerization of the second monomer component in a second exposure region, wherein the second exposure region is exposed to a second light intensity, and wherein the second light intensity is equal to or greater than the first light intensity.

23. The method of claim 22, wherein the first exposure region is exposed to the source of radiation more than once before the second exposure region is exposed to the source of radiation.

24. The method of claim 1, wherein the composite polymer composition comprises an orthodontic appliance.

25. A composite material made by the method of claim 5.

26. The composite material of claim 25, wherein the first polymer comprises a storage modulus at least 200 MPa greater than the storage modulus of the second polymer.

27. The composite material of claim 25, wherein the first polymer comprises a fracture strain that is from 30% to 1,000% greater than the elongation to break of the second polymer.

28. The method of claim 1, wherein the second region has a vertical dimension between 50 µm and 250 µm.

29. The method of claim 1, wherein the first ratio is greater than the resin ratio, and the resin ratio is greater than the second ratio.

* * * * *